US012616453B2

(12) United States Patent
Sung et al.

(10) Patent No.: US 12,616,453 B2
(45) Date of Patent: May 5, 2026

(54) SYSTEM CONFIGURED TO ADJUST SETTING OF ULTRASOUND IMAGE, METHOD OF CONTROLLING THE SYSTEM, AND PROBE INCLUDED IN THE SYSTEM

(71) Applicant: Samsung Medison Co., Ltd., Hongcheon-gun (KR)

(72) Inventors: Jinho Sung, Seoul (KR); Sungjae Lee, Seoul (KR)

(73) Assignee: Samsung Medison Co., Ltd., Hongcheon-gun (KR)

( * ) Notice: Subject to any disclaimer, the term of this patent is extended or adjusted under 35 U.S.C. 154(b) by 0 days.

(21) Appl. No.: 18/628,542

(22) Filed: Apr. 5, 2024

(65) Prior Publication Data

US 2025/0213229 A1 Jul. 3, 2025

(30) Foreign Application Priority Data

Dec. 28, 2023 (KR) ........................ 10-2023-0195382

(51) Int. Cl.
*A61B 8/00* (2006.01)
*G01S 7/52* (2006.01)
*G01S 15/89* (2006.01)

(52) U.S. Cl.
CPC .............. *A61B 8/54* (2013.01); *A61B 8/4477* (2013.01); *A61B 8/4488* (2013.01); *A61B 8/463* (2013.01);
(Continued)

(58) Field of Classification Search
None
See application file for complete search history.

(56) References Cited

U.S. PATENT DOCUMENTS

| 8,043,221 B2 | 10/2011 | Marteau |
| 11,259,777 B2 | 3/2022 | Morikawa |

(Continued)

FOREIGN PATENT DOCUMENTS

| EP | 2205991 A1 | 8/2018 |
| EP | 04233729 A1 | 8/2023 |
| JP | 2016-220739 A | 12/2016 |

OTHER PUBLICATIONS

EESR issued Sep. 13, 2023.
EP Notice of Allowance dated Nov. 20, 2025.

*Primary Examiner* — Nyrobi Celestine
(74) *Attorney, Agent, or Firm* — Harvest IP Law, LLP

(57) ABSTRACT

Provided are an ultrasound imaging system, a method of controlling the ultrasound imaging system, and a probe included in the ultrasound imaging system. The ultrasound imaging system includes a first transducer array and a second transducer array having different specifications, a display configured to display an ultrasound image, an input interface configured to receive a user input related to a setting value of the ultrasound image, and a processor. The processor is configured to identify the setting value of the ultrasound image included in the user input, set an activation transducer array used to generate the ultrasound image among the first transducer array and the second transducer array, based on the setting value, receive the ultrasound data through the activation transducer array, and control the display to display the ultrasound image by using the ultrasound data.

18 Claims, 20 Drawing Sheets

(52) U.S. Cl.
CPC ............ *A61B 8/469* (2013.01); *G01S 7/5209*
(2013.01); *G01S 15/8925* (2013.01); *G01S*
*15/8927* (2013.01)

(56) References Cited

U.S. PATENT DOCUMENTS

| | | | |
|---|---|---|---|
| 2007/0016058 A1 | 1/2007 | Kerwin | |
| 2010/0174189 A1* | 7/2010 | Abraham | ............. A61B 8/4236 |
| | | | 600/439 |
| 2010/0298713 A1* | 11/2010 | Robinson | ........... G01S 15/8909 |
| | | | 600/459 |
| 2013/0172757 A1* | 7/2013 | Frigstad | ................... A61B 8/54 |
| | | | 600/459 |
| 2016/0143619 A1* | 5/2016 | Bae | ........................ A61B 8/461 |
| | | | 600/459 |
| 2017/0143312 A1* | 5/2017 | Hedlund | ............... A61B 6/487 |
| 2019/0033435 A1 | 1/2019 | Sakai | |
| 2019/0254626 A1* | 8/2019 | Corbett | ................. A61B 8/462 |
| 2022/0225964 A1* | 7/2022 | Ikeda | ................. G01S 7/52047 |
| 2023/0263508 A1* | 8/2023 | De Beni | ............... A61B 90/94 |
| | | | 600/437 |

* cited by examiner

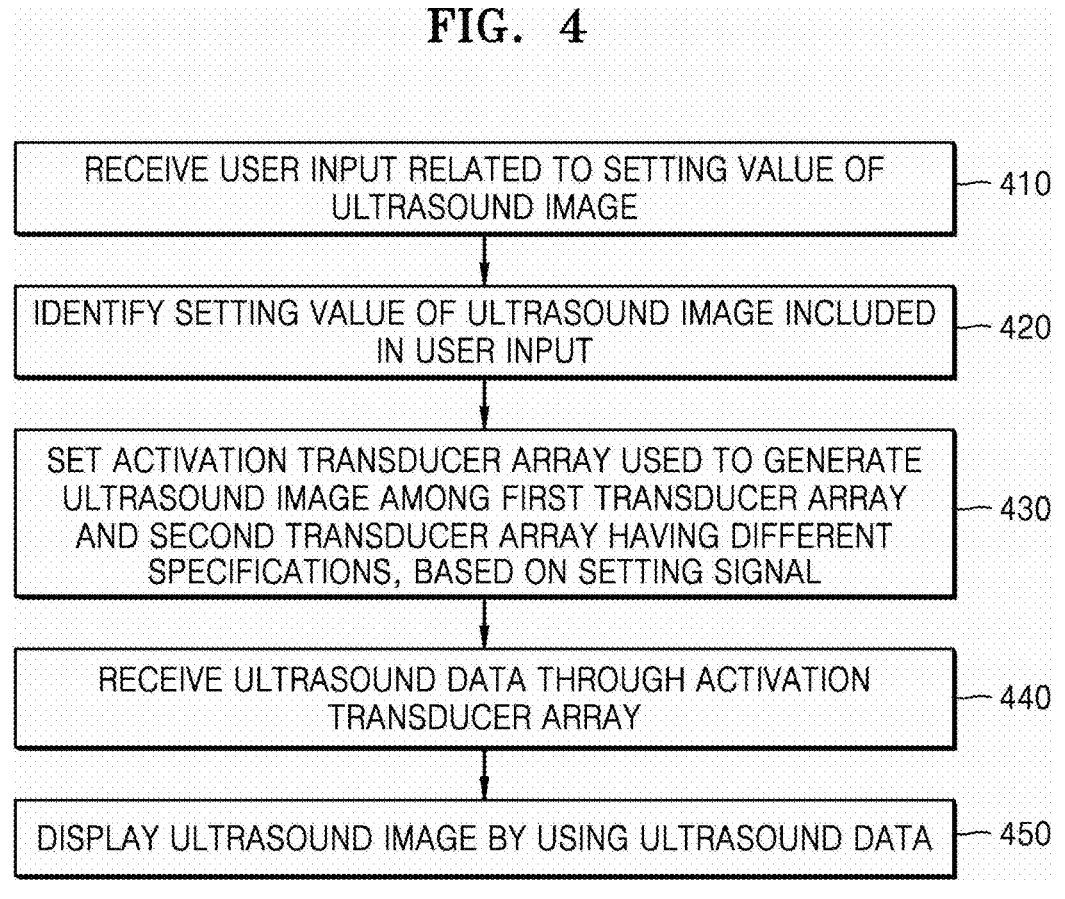

RECEIVE USER INPUT RELATED TO SETTING VALUE OF ULTRASOUND IMAGE —— 410

IDENTIFY SETTING VALUE OF ULTRASOUND IMAGE INCLUDED IN USER INPUT —— 420

SET ACTIVATION TRANSDUCER ARRAY USED TO GENERATE ULTRASOUND IMAGE AMONG FIRST TRANSDUCER ARRAY AND SECOND TRANSDUCER ARRAY HAVING DIFFERENT SPECIFICATIONS, BASED ON SETTING SIGNAL —— 430

RECEIVE ULTRASOUND DATA THROUGH ACTIVATION TRANSDUCER ARRAY —— 440

DISPLAY ULTRASOUND IMAGE BY USING ULTRASOUND DATA —— 450

Figure 11:
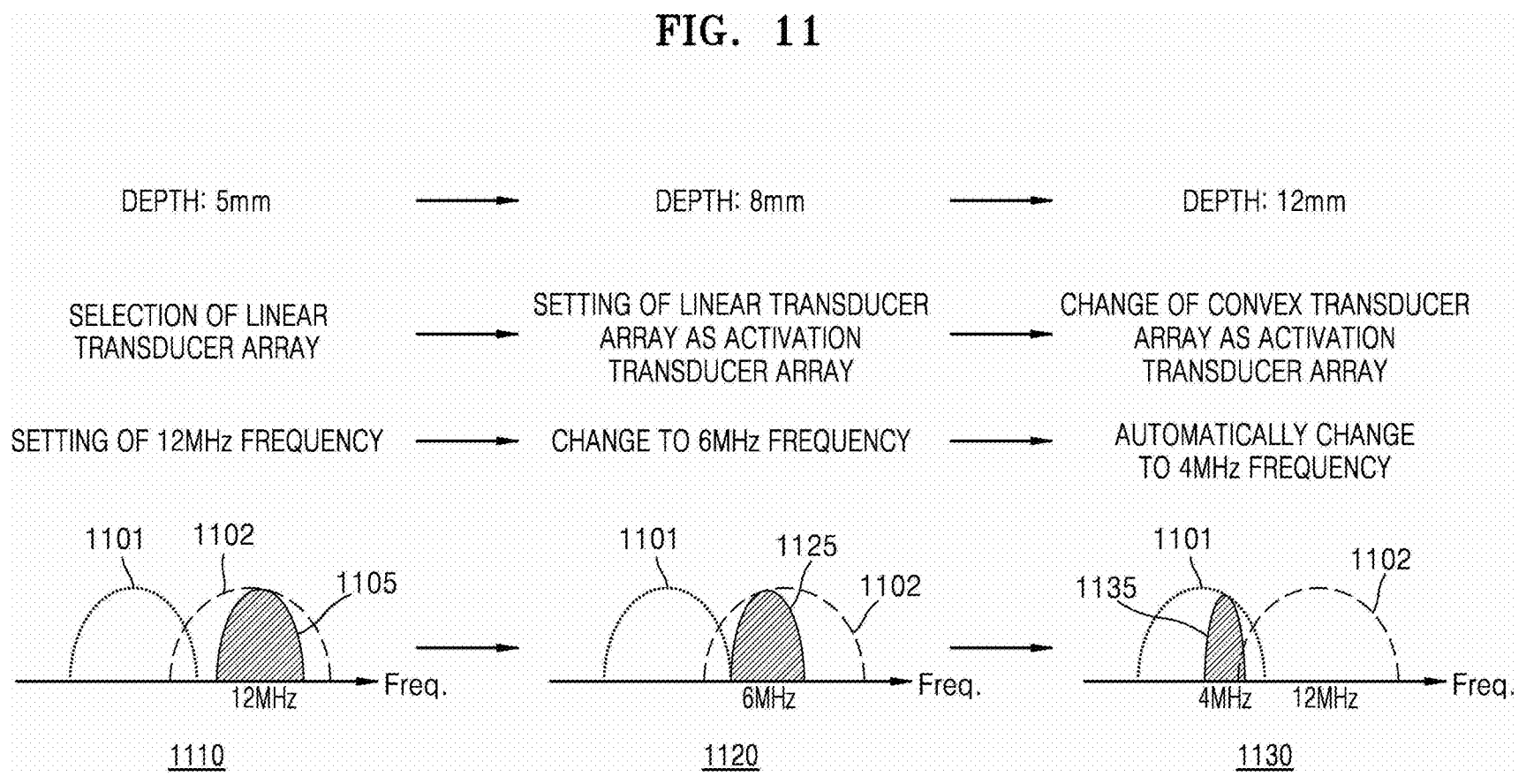

DEPTH: 5mm

SELECTION OF LINEAR
TRANSDUCER ARRAY

SETTING OF 12MHz FREQUENCY

DEPTH: 8mm

SETTING OF LINEAR TRANSDUCER
ARRAY AS ACTIVATION
TRANSDUCER ARRAY

CHANGE TO 6MHz FREQUENCY

DEPTH: 12mm

CHANGE OF CONVEX TRANSDUCER
ARRAY AS ACTIVATION
TRANSDUCER ARRAY

AUTOMATICALLY CHANGE
TO 4MHz FREQUENCY

SYSTEM CONFIGURED TO ADJUST SETTING OF ULTRASOUND IMAGE, METHOD OF CONTROLLING THE SYSTEM, AND PROBE INCLUDED IN THE SYSTEM

CROSS-REFERENCE TO RELATED APPLICATION

This application is based on and claims priority under 35 U.S.C. § 119 to Korean Patent Application No. 10-2023-0195382, filed on Dec. 28, 2023, in the Korean Intellectual Property Office, the disclosure of which is incorporated by reference herein in its entirety.

BACKGROUND

1. Field

The disclosure relates to an ultrasound imaging system, a method of controlling the ultrasound imaging system, and a probe included in the ultrasound imaging system.

2. Description of the Related Art

Recently, in the medical field, various medical imaging apparatuses for imaging information about biological tissue of the human body, for the purpose of early diagnosis of various diseases or surgical operations, are being widely used. Representative examples of such medical imaging apparatuses may include an ultrasound imaging apparatus, a computed tomography (CT) apparatus, and a magnetic resonance imaging (MRI) apparatus.

Ultrasound imaging apparatuses transmit an ultrasound signal generated by a transducer of a probe to an object and receives information regarding a signal reflected by the object, thereby non-invasively obtaining at least one image of a part (e.g., a soft tissue or a blood stream) inside the object. Ultrasound imaging apparatuses may be used for medical purposes, such as observation of the inside of an object, detection of foreign substances inside the object, and diagnosis of damage thereof. Such ultrasound imaging apparatuses have various advantages, including stability, real-time display, and safety because there is no exposure to radiation, compared to X-ray imaging apparatuses, and thus, the ultrasound imaging apparatuses are commonly used together with other imaging apparatuses.

A probe may include a plurality of transducers or a multi-purpose transducer (e.g., a 2D matrix transducer) in order to realize various purposes of an ultrasound imaging apparatus and ensure versatility. The probe may provide a linear array ultrasound image, a convex array ultrasound image, or a phased array ultrasound image to suit a user's purpose. The probe may first set a basic image and then receive a user input for improving image performance. For example, the probe may first set the type of transducer to be activated and then receive a zoom input. The zoom input received by the probe may not affect the type of set transducer. Accordingly, settings for a basic image may be maintained even when the probe receives a user input.

SUMMARY

Additional aspects will be set forth in part in the description which follows and, in part, will be apparent from the description, or may be learned by practice of the presented embodiments of the disclosure.

An ultrasound imaging system according to an embodiment includes a first transducer array and a second transducer array having different specifications, a display configured to display an ultrasound image, based on ultrasound data received through at least one of the first transducer array and the second transducer array, an input interface configured to receive a user input related to a setting value of the ultrasound image, and a processor. The processor is configured to identify the setting value of the ultrasound image included in the user input, set an activation transducer array used to generate the ultrasound image among the first transducer array and the second transducer array, based on the setting value, receive the ultrasound data through the activation transducer array, and control the display to display the ultrasound image by using the ultrasound data.

A method of controlling an ultrasound imaging system, according to an embodiment, includes receiving a user input related to a setting value of an ultrasound image, identifying the setting value of the ultrasound image included in the user input, setting an activation transducer array used to generate the ultrasound image among a first transducer array and a second transducer array having different specifications, based on the setting value, receiving ultrasound data through the activation transducer array, and displaying the ultrasound image by using the ultrasound data.

BRIEF DESCRIPTION OF THE DRAWINGS

This disclosure may be readily understood by reference to the following detailed description and the accompanying drawings, in which reference numerals refer to structural elements.

The above and other aspects, features, and advantages of certain embodiments of the disclosure will be more apparent from the following description taken in conjunction with the accompanying drawings, in which:

Figure 1A:
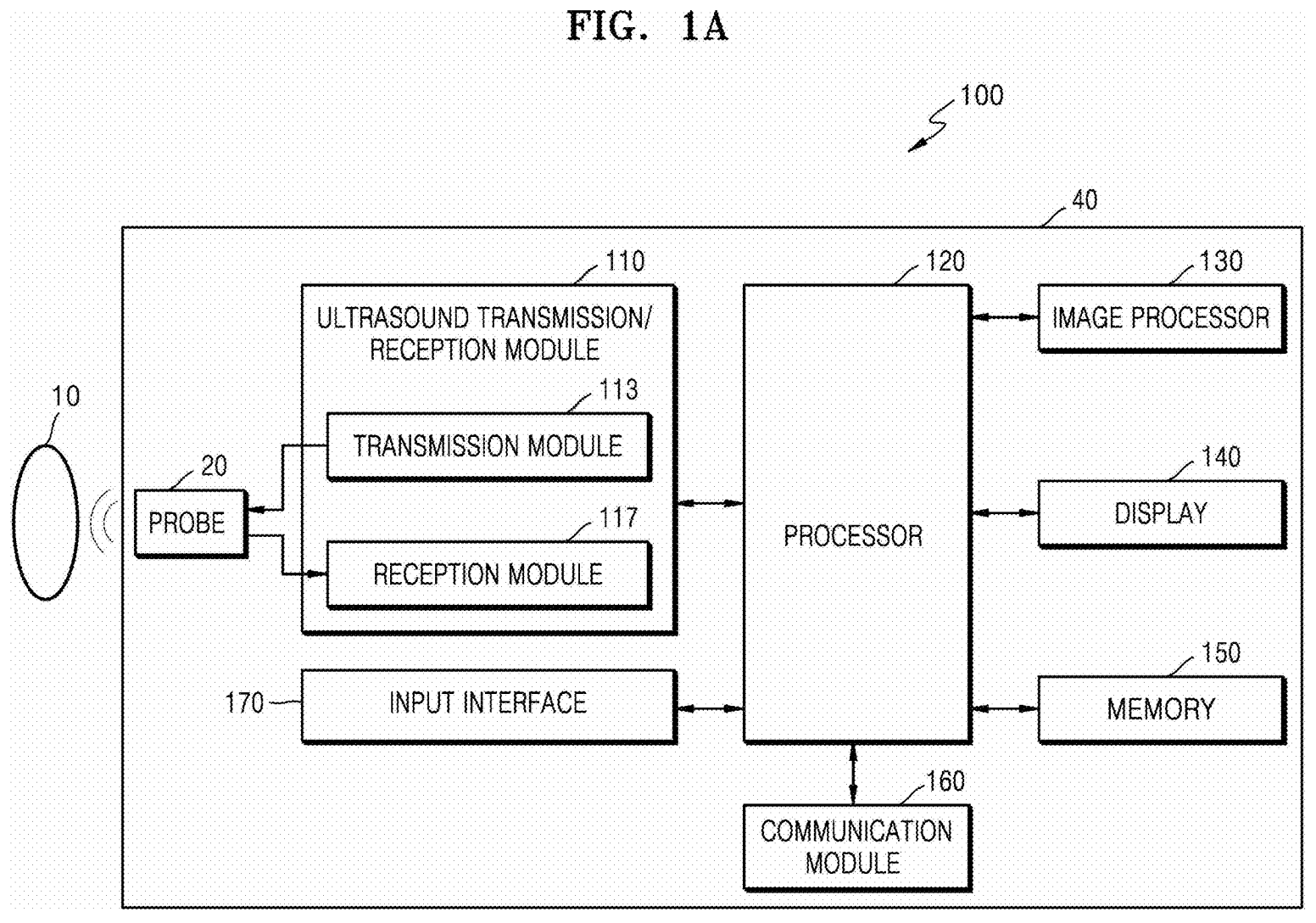

FIGS. 1A and 1B are block diagrams of an ultrasound imaging system according to an embodiment;

FIG. 4 is a flowchart of a method of controlling an ultrasound imaging system, according to an embodiment;

FIG. 11 is a diagram illustrating an ultrasound imaging system, according to an embodiment, setting a frequency spectrum or an activation transducer array when changing the depth of an ultrasound image;

DETAILED DESCRIPTION

Figure 1B:
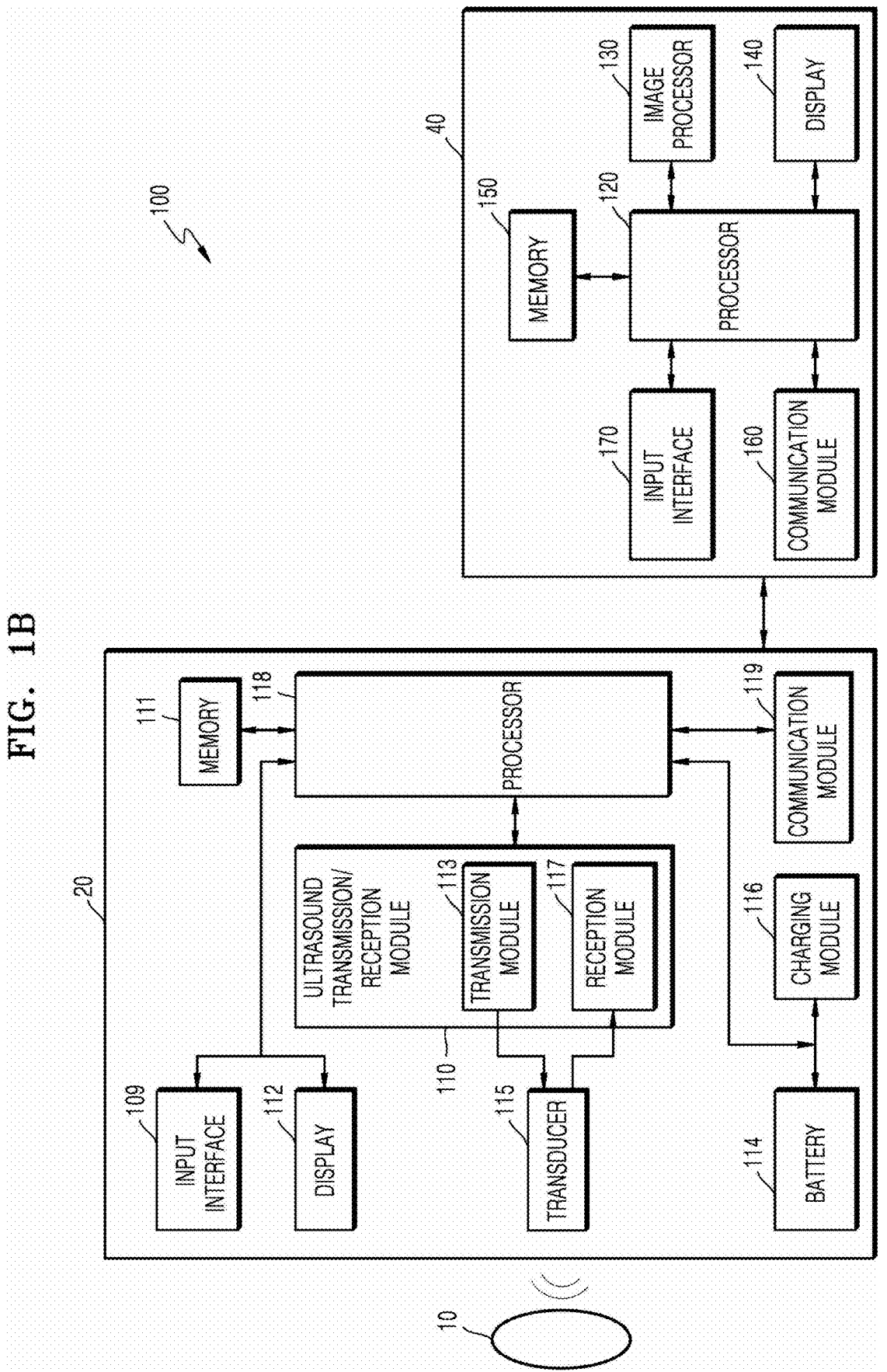

The principle of the disclosure is explained and embodiments are disclosed so that the scope of the disclosure is clarified and one of ordinary skill in the art to which embodiments pertain implements embodiments. Embodiments may have various forms.

Throughout the specification, like reference numerals or characters refer to like elements. In the present specification, all elements of embodiments are not explained, but general matters in the technical field of the disclosure or redundant matters between embodiments will not be described. The term "module" or "unit" used herein may be implemented as one or more of software, hardware, or firmware. According to embodiments, a plurality of "modules" or "units" may be implemented as one element, or one "module" or "unit" may include a plurality of elements.

The singular form of a noun corresponding to an item may include one item or a plurality of items, unless a relevant context clearly dictates otherwise.

Each of expressions "A or B", "at least one of A and B", "at least one of A or B", and "one or more of A and/or B", "A, B, or C," "at least one of A, B, and C", and "at least one of A, B, or C" may include any one of listed items and all of at least one combination of the items.

The term "and/or" used herein includes any and all combinations of one or more of the associated listed items.

The terms such as "first", "second", "primarily", or "secondary" used herein may represent various elements regardless of order and/or importance, and do not limit corresponding elements. These terms may be used for distinguishing one element from another element.

Terms such as 'front surface', 'rear surface', 'upper surface', 'lower surface', 'side surface', 'left side', 'right side', 'upper', and 'lower' used herein are defined based on the drawings, and the shape and location of each component are not limited by these terms.

The terms such as "including," "having," and "comprising" used herein are intended to indicate the existence of the features, numbers, steps, actions, components, parts, or combinations thereof mentioned in the disclosure, and are not intended to preclude the possibility that one or more other features, numbers, steps, actions, components, parts, or combinations thereof may exist or may be added.

When a component is said to be "connected to", "coupled to", "supported by" or "contact" another component, this may include not only a case where the components are directly connected to, coupled to, supported by, or contact each other, but also a case where the components are indirectly connected to, coupled to, supported by, or contact with each other through a third component.

When a component is said to be located "on" another component, this includes not only a case in which a component is in contact with another component, but also a case in which another component exists between two components.

Ultrasound apparatuses according to various embodiments will now be described in detail with reference to the attached drawings. In the drawings, like elements are denoted by like reference numerals, and a repeated explanation thereof will not be given.

An image used herein may be a medical image captured by a medical imaging apparatus, such as a magnetic resonance imaging (MRI) apparatus, a computed tomography (CT) apparatus, an ultrasound imaging apparatus, or an X-ray imaging apparatus.

Throughout the specification, a term 'object' is a thing to be imaged, and may include a human, an animal, or a part of a human or animal. For example, the object may include a part of a body (i.e., an organ), a phantom, or the like.

In the disclosure, an "ultrasound image" refers to an image of an object generated or processed based on ultrasound signals transmitted to the object and reflected therefrom.

Embodiments will now be described in detail with reference to the accompanying drawings.

FIGS. 1A and 1B are block diagrams of an ultrasound imaging system 100 according to an embodiment.

Referring to FIGS. 1A and 1B, the ultrasound imaging system 100 may include a probe 20 and an ultrasound imaging apparatus 40.

The ultrasound imaging apparatus 40 may be not only a cart type apparatus, but also a portable apparatus. Examples of portable ultrasound imaging apparatuses may include, but are not limited to, a smartphone, a laptop computer, a personal digital assistant (PDA), and a tablet PC, each including a probe and an application. The ultrasound imaging apparatus 40 may also be implemented as an integrated probe.

The probe 20 may include a wired probe that is connected to the ultrasound imaging apparatus 40 by wire to communicate with the ultrasound imaging apparatus 40 by wire, a wireless probe that is wirelessly connected to the ultrasound imaging apparatus 40 to communicate wirelessly with the ultrasound imaging apparatus 40, and/or a hybrid probe that is connected to the ultrasound imaging apparatus 40 by wire or wirelessly to communicate with the ultrasound imaging apparatus 40 by wire or wirelessly.

According to various embodiments, the ultrasound imaging apparatus 40 may include an ultrasound transmission/reception module 110 as shown in FIG. 1A, or the probe 20 may include the ultrasonic transmission/reception module 110 as shown in FIG. 1B. According to various embodiments, the ultrasound imaging apparatus 40 and the probe 20 may include the ultrasound transmission/reception module 110.

According to various embodiments, the probe 20 may further include at least one of an image processor 130, a display 140, or an input interface 170, or a combination thereof. In the disclosure, a description of the ultrasound transmission/reception module 110, the image processor 130, the display 140, or the input interface 170 included in the ultrasound imaging apparatus 40 is also applicable to the ultrasound transmission/reception module 110, the image processor 130, the display 140, or the input interface 170 included in the ultrasound imaging apparatus 40.

FIG. 1A is a block diagram of a configuration of the ultrasound imaging system 100 when the probe 20 is a wired probe or a hybrid probe.

The probe 20 may include a plurality of transducers. The plurality of transducers may be arranged in a predetermined configuration to be implemented as a transducer array. The transducer array may correspond to a one-dimensional (1D) array or a two-dimensional (2D) array. The plurality of transducers may transmit an ultrasound signal to an object 10 according to a transmission signal applied by a transmission module 113 included in the ultrasound transmission/reception module 110. The plurality of transducers may receive an ultrasound signal (echo signal) reflected by the object 10 to form a reception signal. The probe 20 may be integrated with the ultrasound imaging apparatus 40, or may be separate from the ultrasound imaging apparatus 40 and may be connected thereto via a wired communication. The ultrasound imaging apparatus 40 may be connected to one probe 20 or a plurality of probes 20 according to embodiments.

When the probe 20 is a wired probe or a hybrid probe, the probe 20 may include a cable and a connector both connectable to a connector of the ultrasound imaging apparatus 40.

The probe 20 according to an embodiment may be implemented as a 2D probe. When the probe 20 is implemented as a 2D probe, the plurality of transducers included in the probe 20 may be arranged in two dimensions to form a 2D transducer array.

For example, the 2D transducer array may include a plurality of sub-arrays arranged in a second direction different from a first direction and each including a plurality of transducers arranged in the first direction.

When the probe 20 according to an embodiment is implemented as a 2D probe, the ultrasound transmission/reception module 110 may include at least one of an analog beamformer or a digital beamformer. According to an embodiment, the 2D probe may include at least one of an analog beamformer or a digital beamformer, or a combination thereof, according to implementation types.

The processor 120 controls the transmission module 113 to form a transmission signal that is to be applied to each of the plurality of transducers 115, considering respective positions and focal points of the plurality of transducers included in the probe 20.

The processor 120 may control a reception module 117 to generate ultrasonic data by performing analog-to-digital conversion on a reception signal received from the probe 20 and summing a digital reception signal considering the respective positions and focus points of the plurality of transducers.

When the probe 20 is implemented as a 2D probe, the processor 120 may calculate a time delay value for digital beamforming for each sub-array with respect to each of the plurality of sub-arrays included in the 2D transducer array. The processor 120 may calculate a time delay value for analog beamforming with respect to each of the plurality of transducer included in one of the plurality of sub-arrays. The processor 120 may control the analog beamformer and the digital beamformer to form a transmission signal that is to be applied to each of the plurality of transducers, according to the time delay value for analog beamforming and the time delay value for digital beamforming. The processor 120 may control the analog beamformer to sum signals received from the plurality of transducers for each sub-array according to the time delay value for analog beamforming. The processor 120 may control the ultrasound transmission/reception module 110 to perform analog-to-digital conversion with respect to a result of the summation of the signals for each sub-array. The processor 120 may control the digital beamformer to generate ultrasound data, by summing digital signals according to the time delay value for digital beamforming.

The image processor 130 generates or processes an ultrasound image by using the generated ultrasound data.

The display 140 may display the generated ultrasound image, and various pieces of information processed by the ultrasound imaging apparatus 40 or the probe 20. The probe 20 or the ultrasound imaging apparatus 40 may include one display 140 or a plurality of displays 140 according to implementation types. The display 140 may include a touch panel or touch screen. The display 140 may include a flexible display.

The processor 120 may control an overall operation of the ultrasound imaging apparatus 40 and may control operations of the components of the ultrasound imaging apparatus 40. The processor 120 may perform or control various operations or functions of the ultrasound imaging apparatus 40 by executing programs or instructions stored in the memory 150. The processor 120 may receive a control signal from the input interface 170 or an external device to control an operation of the ultrasound imaging apparatus 40.

The ultrasound imaging apparatus 40 may include a communication module 160, and may be connected to and communicate with external devices (e.g., the probe 20, a server, a medical apparatus, and a portable device (smartphone, tablet personal computer (PC), wearable device, etc.), via the communication module 160.

The communication module 160 may include at least one component that enables communication with the external devices. The communication module 160 may include, for example, at least one of a close-distance communication module, a wired communication module, or a wireless communication module.

The communication module 160 may receive a control signal or data from an external device. The processor 120 may control an operation of the ultrasound imaging apparatus 40 according to the control signal received through the communication module 160. By transmitting the control signal to the external device via the communication module 160, the processor 120 may control the external device according to the transmitted control signal. The external device may operate according to the control signal received from the ultrasound imaging apparatus 40, or process data received from the ultrasound imaging apparatus 40.

A program or application related to the ultrasound imaging apparatus 40 may be installed in the external device. The program or application installed in the external device may control the ultrasonic imaging apparatus 40, or may operate according to the control signal or data received from the ultrasonic imaging apparatus 40.

The external device may receive or download the program or application related to the ultrasound imaging apparatus 40 from the ultrasound imaging apparatus 40, the probe 20, or a server, and may provide and execute the program or application in the external device. The ultrasound imaging apparatus 40, the probe 20, or the server providing the program or application may include a recording medium that stores instructions, commands, installation files, executable files, or related data of the program or application. The external device may also be sold with programs or applications provided.

The memory 150 may store various pieces of data or various programs for driving and controlling the ultrasound imaging apparatus 40, input/output ultrasound data, ultrasound images, etc.

The input interface 170 may receive a user input for controlling the ultrasound imaging apparatus 40. For example, the user input may include, but is not limited to, an input for manipulating a button, a key pad, a mouse, a trackball, a jog switch, a knop, or the like, an input for touching a touch pad or a touch screen, a voice input, a motion input, and a biometric data input (e.g., iris recognition and fingerprint recognition).

FIG. 1B is a block diagram showing control by the ultrasound imaging system 100 when the probe 20 is a wired probe or a hybrid probe.

Of course, according to various embodiments, the ultrasound imaging apparatus 40 shown in FIG. 1B may be replaced by the ultrasound imaging apparatus 40 described above with reference to FIG. 1A.

Of course, according to various embodiments, the probe 20 shown in FIG. 1A may be replaced by the probe 20 described above with reference to FIG. 1B.

The probe 20 may include a display 112, a transmission module 113, a battery 114, a transducer 115, a charging module 116, a reception module 117, an input interface 109, a processor 118, and a communication module 119. In FIG. 1B, the probe 20 is shown as including both the transmission module 113 and the reception module 117. However, according to implementation types, the probe 20 may include only some of the transmission module 113 and the reception module 117, or some of the transmission module 113 and the reception module 117 may be included in the ultrasound imaging apparatus 40. According to an embodiment, the probe 20 may further include an image processor 130.

The transducer 115 may include a plurality of transducers. The plurality of transducers may be arranged in a predetermined configuration to be implemented as a transducer array. The transducer array may correspond to a one-dimensional (1D) array or a two-dimensional (2D) array. The plurality of transducers may transmit an ultrasound signal to the object 10 according to a transmission signal applied by the transmission module 113. The plurality of transducers may receive an ultrasound signal reflected by the object 10 and may form or generate an electrical reception signal.

The charging module 116 may charge the battery 114. The charging module 116 may receive power from an external source. According to an embodiment, the charging module 116 may receive power wirelessly. According to an embodiment, the charging module 116 may receive power by wire. The charging module 116 may transmit the received power to the battery 114.

The processor 118 controls the transmission module 113 to generate or form a transmission signal that is to be applied to each of the plurality of transducers 115, considering respective positions and focal points of the plurality of transducers.

The processor 118 may control the reception module 117 to generate ultrasonic data by performing analog-to-digital conversion on a reception signal received from the transducer 115 and summing a digital reception signal considering the respective positions and focus points of the plurality of transducers. According to an embodiment, when the probe 20 includes the image processor 130, the probe 20 may generate an ultrasound image by using the generated ultrasound data.

When the probe 20 is implemented as a 2D probe, the processor 118 may calculate a time delay value for digital beamforming for each sub-array with respect to each of the plurality of sub-arrays included in the 2D transducer array. The processor 118 may calculate a time delay value for analog beamforming with respect to each of the plurality of transducer included in one of the plurality of sub-arrays. The processor 118 may control the analog beamformer and the digital beamformer to form a transmission signal that is to be applied to each of the plurality of transducers, according to the time delay value for analog beamforming and the time delay value for digital beamforming. The processor 118 may control the analog beamformer to sum signals received from the plurality of transducers for each sub-array according to the time delay value for analog beamforming. The processor 118 may control the ultrasound transmission/reception module 110 to perform analog-to-digital conversion with respect to a result of the summation of the signals for each sub-array. The processor 118 may control the digital beamformer to generate ultrasound data, by summing digital signals according to the time delay value for digital beamforming.

The processor 118 may control an overall operation of the probe 20 and may control operations of the components of the probe 20. The processor 118 may perform or control various operations or functions of the probe 20 by executing programs or instructions stored in the memory 111. The processor 118 may receive a control signal from the input interface 109 of the probe 20 or an external device (e.g., the ultrasound imaging apparatus 40) to control an operation of the probe 20. The processor 118 may receive a control signal from the input interface 109 or the external device to control an operation of the probe 20. The input interface 109 may receive a user input for controlling the probe 20. For example, the user input may include, but is not limited to, an input for manipulating a button, a key pad, a mouse, a trackball, a jog switch, a knop, or the like, an input for touching a touch pad or a touch screen, a voice input, a motion input, and a biometric data input (e.g., iris recognition and fingerprint recognition).

The display 112 displays an ultrasound image generated by the probe 20, an ultrasound image generated by processing ultrasound data generated by the probe 20, an ultrasound image received from the ultrasound imaging apparatus 40, or various pieces of information that are processed by the ultrasound imaging system 100. The display 112 may further display status information of the probe 20. The status information of the probe 20 may include device information of the probe 20, battery status information of the probe 20, frequency band information of the probe 20, output information of the probe 20, information regarding occurrence or non-occurrence of abnormality of the probe 20, setting information of the probe 20, or temperature information of the probe 20.

The probe 20 may include one display 112 or a plurality of displays 112 according to implementation types. The display 112 may include a touch panel or touch screen. The display 112 may include a flexible display.

The communication module 119 may wirelessly transmit the generated ultrasound data or ultrasound image to the ultrasound imaging apparatus 40 through a wireless network. The communication module 119 may receive a control signal or data from the ultrasound imaging apparatus 40.

The ultrasound imaging apparatus 40 may receive ultrasound data or the ultrasound image from the probe 20.

According to an embodiment, when the probe 20 includes the image processor 130 capable of generating an ultrasound image by using ultrasound data, the probe 20 may transmit the ultrasound image generated by the image processor 130 or the ultrasound data to the ultrasound imaging apparatus 40.

According to an embodiment, when the probe 20 does not include the image processor 130 capable of generating an ultrasound image by using ultrasound data, the probe 20 may transmit the ultrasound data to the ultrasound imaging apparatus 40. The ultrasound data may include ultrasound raw data, and the ultrasound image may refer to ultrasound image data.

The ultrasound imaging apparatus 40 may include a processor 120, an image processor 130, a display 140, a memory 150, a communication module 160, and an input interface 170.

The image processor 130 generates or processes the ultrasound image by using the ultrasound data received from the probe 20.

The display 140 may display the ultrasound image received from the probe 20, the ultrasound image generated by processing the ultrasound data received from the probe 20, or various pieces of information that are processed by the ultrasound imaging system 100. The ultrasound imaging apparatus 40 may include one display 140 or a plurality of displays 140 according to implementation types. The display 140 may include a touch panel or touch screen. The display 140 may include a flexible display.

The processor 120 may control an overall operation of the ultrasound imaging apparatus 40 and may control operations of the components of the ultrasound imaging apparatus 40. The processor 120 may perform or control various operations or functions of the ultrasound imaging apparatus 40 by executing programs or instructions stored in the memory 150. The processor 120 may receive a control signal from the input interface 170 or an external device to control an operation of the ultrasound imaging apparatus 40.

The ultrasound imaging apparatus 40 may include a communication module 160, and may be connected to and communicate with external devices (e.g., the probe 20, a server, a medical apparatus, and a portable device (smartphone, tablet personal computer (PC), wearable device, etc.), via the communication module 160.

The communication module 160 may include at least one component that enables communication with the external devices. The communication module 160 may include, for example, at least one of a close-distance communication module, a wired communication module, or a wireless communication module.

The communication module 160 of the ultrasonic imaging apparatus 40 and the communication module 119 of the probe 20 may communicate using a network or using a short-range wireless communication method. For example, the communication module 160 of the ultrasonic imaging apparatus 40 and the communication module 119 of the probe 20 may communicate with each other by using one of wireless data communication methods including, for example, a wireless LAN, Wi-Fi, Bluetooth, Zigbee, Wi-Fi Direct (WFD), infrared communication (IrDA), Bluetooth Low Energy (BLE), Near Field Communication (NFC), Wireless Broadband Internet (Wibro), World Interoperability for Microwave Access (WiMAX), a shared wireless access protocol (SWAP), Wireless Gigabit Alliance (Wi-Gig), RF communication, and 60 GHz millimeter (mm) wave short-range communication.

To this end, the communication module 160 of the ultrasonic imaging apparatus 40 and the communication module 119 of the probe 20 may include at least one of a wireless LAN communication module, a Wi-Fi communication module, a Bluetooth communication module, a Zigbee communication module, a WFD communication module, an IrDA communication module, a BLE communication module, an NFC communication module, a Wibro communication module, a WiMAX communication module, a SWAP communication module, a WiGig communication module, an RF communication module, or a 60 GHz mm wave short-range communication module.

According to an embodiment, the probe 20 may transmit device information (e.g., ID information) of the probe 20 to the ultrasound imaging apparatus 40 by using a first communication method (e.g., BLE), and may be paired wirelessly with the ultrasound imaging apparatus 40. The probe 20 may transmit the ultrasound data and/or the ultrasound image to the paired ultrasound imaging apparatus 40.

The device information of the probe 20 may include various pieces of information related to a serial number, model name, or battery status of the probe 20.

The ultrasound imaging apparatus 40 may receive the device information (e.g., ID information) of the probe 20 from the probe 20 by using the first communication method (e.g., BLE), and may be paired wirelessly with the probe 20. The ultrasound imaging apparatus 40 may transmit an activation signal to the paired probe 20 and may receive the ultrasound data and/or the ultrasound image from the probe 20. In this case, the activation signal may include a signal for controlling an operation of the probe 20.

According to an embodiment, the probe 20 may transmit the device information (e.g., ID information) of the probe 20 to the ultrasound imaging apparatus 40 by using the first communication method (e.g., BLE), and may be paired wirelessly with the ultrasound imaging apparatus 40. The probe 20 may transmit the ultrasound data and/or the ultrasound image to the ultrasound imaging apparatus 40 paired with the probe 20 by using the first communication method, by using a second communication method (e.g., 60 GHz mm waves or Wi-Fi).

The ultrasound imaging apparatus 40 may receive the device information (e.g., ID information) of the probe 20 from the probe 20 by using the first communication method (e.g., BLE), and may be paired wirelessly with the probe 20. The ultrasound imaging apparatus 40 may transmit an activation signal to the paired probe 20, and may receive the ultrasound data and/or the ultrasound image from the probe 20 by using the second communication method (e.g., 60 GHz mm waves or Wi-Fi).

According to an embodiment, the first communication method used to pair the probe 20 with the ultrasound imaging apparatus 40 may have a lower frequency band than a frequency band of the second communication method used by the probe 20 to transmit the ultrasound data and/or the ultrasound image to the ultrasound imaging apparatus 40.

The display 140 of the ultrasound imaging apparatus 40 may display user interfaces (UIs) indicating the device information of the probe 20. For example, the display 140 may display a UI or the like indicating identification information of the probe 20, a pairing method indicating a pairing method with the probe 20, a data communication status between the probe 20 and the ultrasound imaging apparatus 40, a method of performing data communication with the ultrasound imaging apparatus 40, or the battery status of the probe 20.

When the probe 20 includes the display 112, the display 112 of the probe 20 may display a UI indicating the device information of the probe 20. For example, the display 112 may display a UI or the like indicating identification information of the probe 20, a pairing method indicating a pairing method with the probe 20, a data communication status between the probe 20 and the ultrasound imaging apparatus 40, a method of performing data communication with the ultrasound imaging apparatus 40, or the battery status of the probe 20.

The communication module 160 may receive a control signal or data from an external device. The processor 120 may control an operation of the ultrasound imaging apparatus 40 according to the control signal received through the communication module 160.

By transmitting the control signal to the external device via the communication module 160, the processor 120 may control the external device according to the transmitted control signal. The external device may operate according to the control signal received from the ultrasound imaging apparatus 40, or process data received from the ultrasound imaging apparatus 40.

The external device may receive or download the program or application related to the ultrasound imaging apparatus 40 from the ultrasound imaging apparatus 40, the probe 20, or a server, and may provide and execute the program or application in the external device. The ultrasound imaging apparatus 40, the probe 20, or the server providing the program or application may include a recording medium that stores instructions, commands, installation files, executable files, or related data of the program or application. The external device may also be sold with programs or applications provided.

The memory 150 may store various pieces of data or various programs for driving and controlling the ultrasound imaging apparatus 40, input/output ultrasound data, ultrasound images, etc.

An example of the ultrasound imaging system 100 according to an embodiment will now be described with reference to FIGS. 2A, 2B, 2C, and 2D.

FIGS. 2A, 2B, 2C, and 2D are views illustrating an ultrasound imaging apparatus 100 according to an embodiment.

Figure 2A:
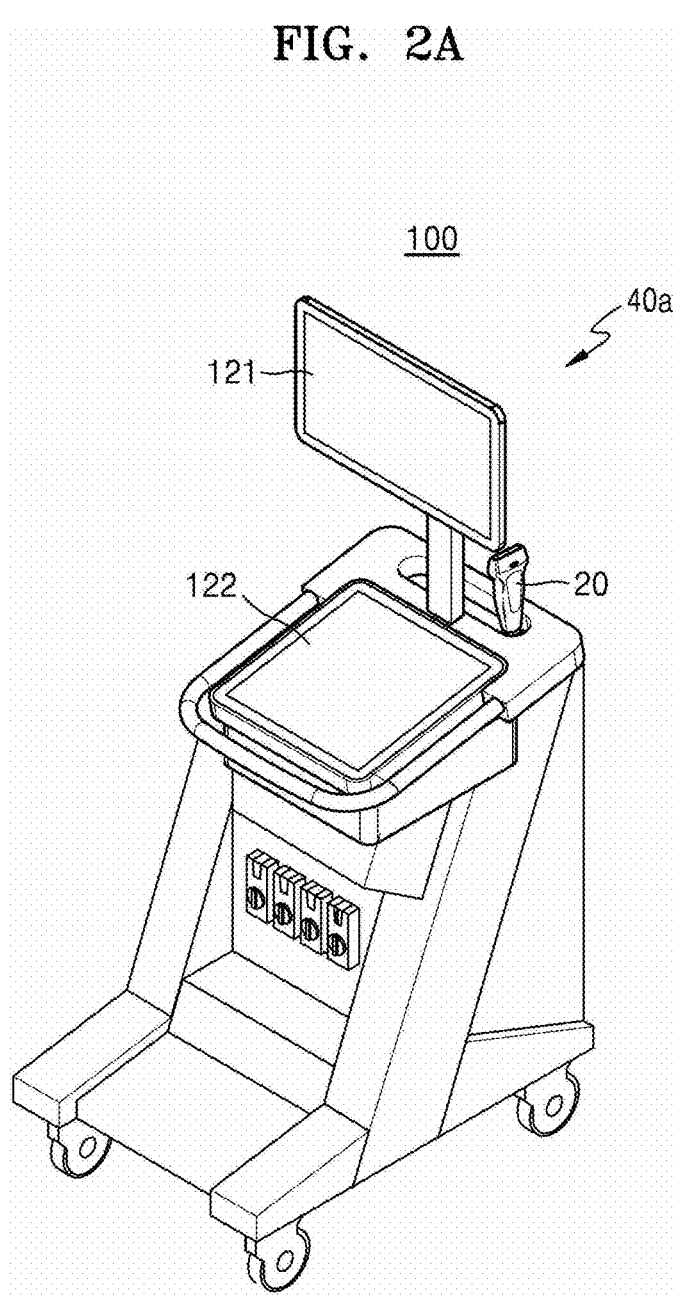
FIGS. 2A, 2B, 2C, and 2D are views illustrating an ultrasound imaging apparatus according to an embodiment.
Figure 2B:
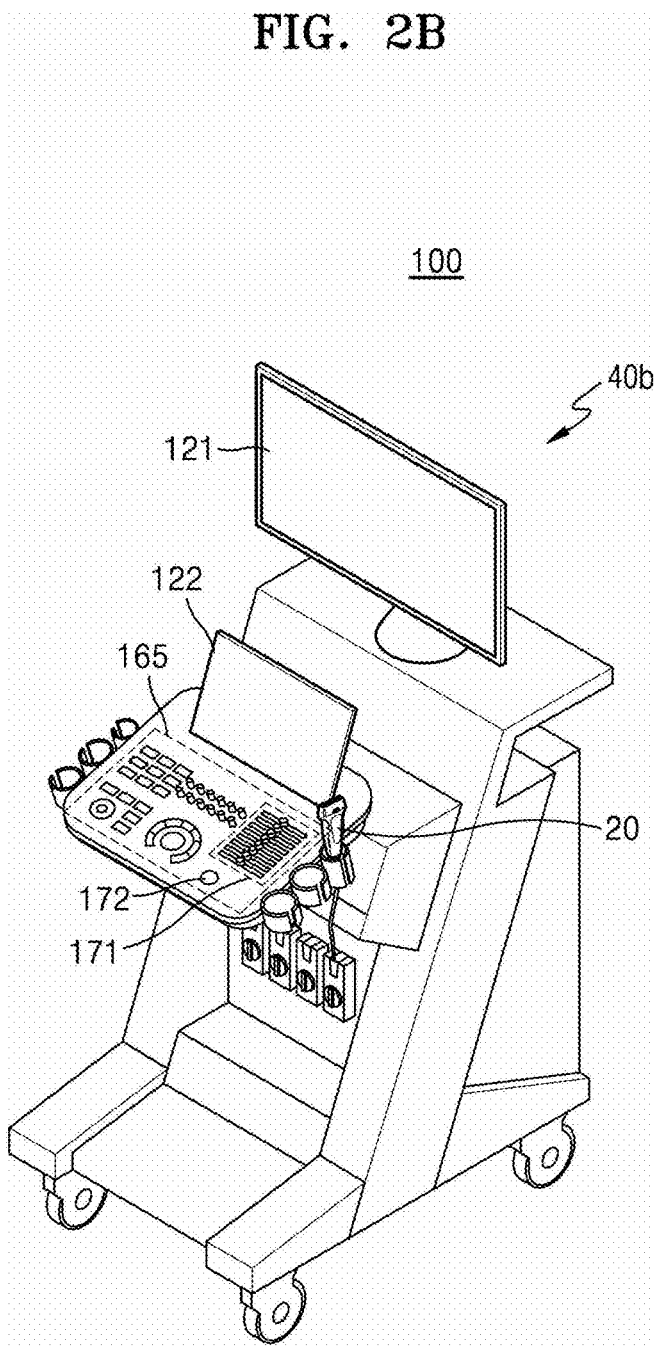

Referring to FIGS. 2A and 2B, ultrasound imaging apparatuses 40a and 40b may include a main display 121 and a sub-display 122. The main display 121 and the sub-display 122 may correspond to the display 140 of FIGS. 1A and 1B. At least one of the main display 121 or the sub-display 122 may be implemented using a touch screen. At least one of the main display 121 or the sub-display 122 may display various pieces of information that are processed by the ultrasound imaging apparatuses 40a and 40b, or an ultrasound image. At least one of the main display 121 or the sub-display 122 may be implemented using a touch screen, and may provide a graphical user interface (GUI) to thereby receive data for controlling the ultrasound imaging apparatuses 40a and 40b from a user. For example, the main display 121 may display an ultrasound image, and the sub-display 122 may display a control panel for controlling display of the ultrasound image, in a GUI form. The sub-display 122 may receive data for controlling display of an image, via a control panel displayed in a GUI form. For example, a Time Gain Compensation (TGC) button, a Lateral Gain Compensation (LGC) button, a Freeze button, a trackball, a jog switch, or a knob may be provided as a GUI on the sub-display 122.

The ultrasound imaging apparatuses 40a and 40b may control display of an ultrasound image displayed on the main display 121, by using the received control data. The ultrasound imaging apparatuses 40a and 40b may be connected to the probe 20 by wire or wirelessly to transmit and receive ultrasound signals to an object.

Referring to FIG. 2B, the ultrasound imaging apparatus 40b may further include a control panel 165 in addition to the main display 121 and the sub-display 122. The control panel 165 may include buttons, a trackball, a jog switch, a knob, etc., and may receive data for controlling the ultrasonic imaging apparatus 40b from the user. For example, the control panel 165 may include a TGC button 171, a Freeze button 172, etc. The TGC button 171 is a button for setting a TGC value for each depth of an ultrasound image. When an input of the Freeze button 172 is detected while an ultrasound image is being scanned, the ultrasound imaging apparatus 40b may maintain the display of a frame image at this point of time, capture the frame image at this point of time, or store the frame image at this point of time.

The buttons, the trackball, the jog switch, the knob, etc. included in the control panel 165 may be provided as a GUI on the main display 121 or sub-display 122. The ultrasound imaging apparatuses 40a and 40b may be connected to the probe 20 to transmit and receive ultrasound signals to an object.

The ultrasonic imaging apparatuses 40a and 40b may include various types of input/output interfaces such as a speaker, an LED, and a vibration device. For example, the ultrasonic imaging apparatuses 40a and 40b may output various pieces of information in the form of graphics, sound, or vibration through an input/output interface. The ultrasound imaging apparatuses 40a and 40b may output various notifications or data through input/output interfaces.

Figure 2C:
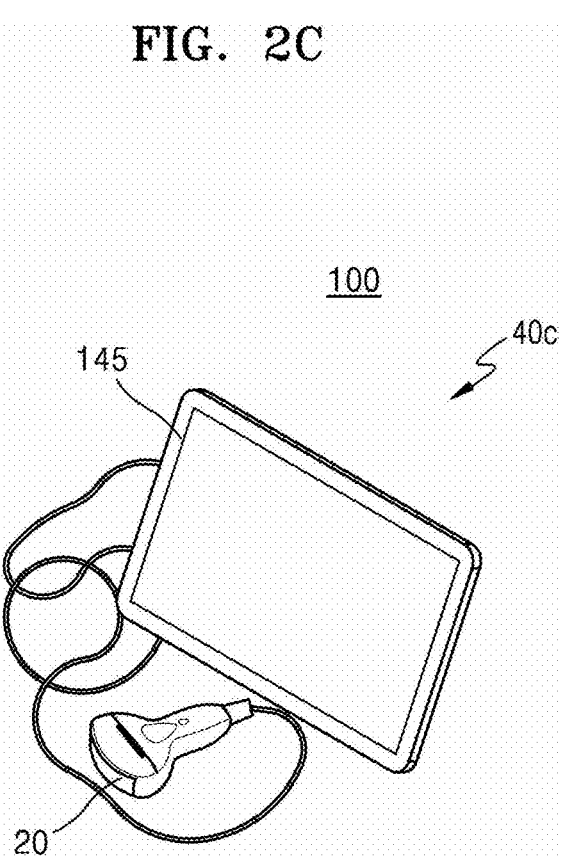
Figure 2D:
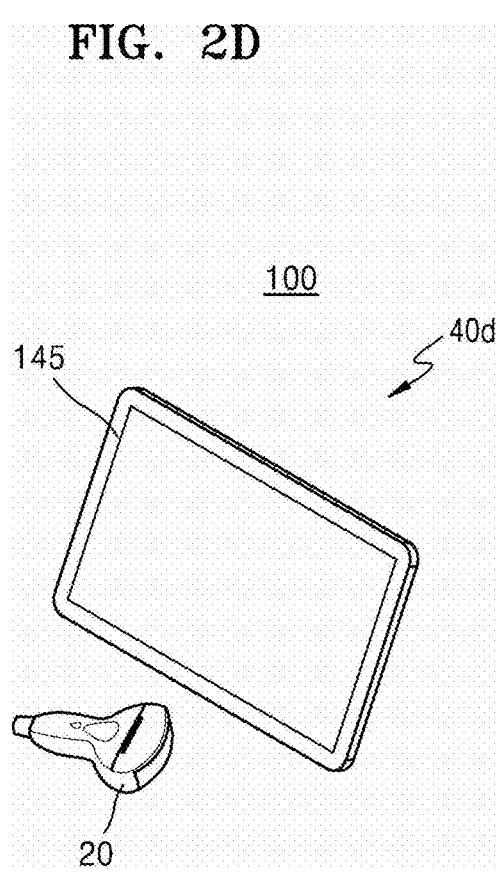

Referring to FIGS. 2C and 2D, ultrasound imaging apparatuses 40c and 40d may be implemented as portable devices. Examples of the ultrasound imaging apparatuses 40c and 40d may include, but are not limited to, a smartphone, a laptop computer, a personal digital assistant (PDA), or a tablet PC each including a probe and an application.

The ultrasound imaging apparatus 40c may include a main body 145. Referring to FIG. 2C, the probe 20 may be connected to one side of the main body 145 by wire. To this end, the main body 145 may include a connection terminal from which a cable connected to the probe 20 is detachable. The probe 20 may include a cable including a connection terminal connectable to the main body 145.

Referring to FIG. 2D, the probe 20 may be wirelessly connected to the ultrasound imaging apparatus 40d. The main body 145 may include an input/output interface (e.g., a touch screen). The input/output interface may display, for example, ultrasound images, various pieces of information processed by an ultrasound imaging apparatus, or a GUI.

The ultrasound imaging apparatus 40d and the probe 20 may establish communication or be paired, according to short-range wireless communication. For example, the ultrasound imaging apparatus 40d and the probe 20 may perform communication by using Bluetooth, BLE, Wi-Fi, Wi-Fi Direct, or the like.

The ultrasound imaging apparatuses 40c and 40d may execute a program or application related to the probe 20 to control the probe 20 and output information related to the probe 20. The ultrasound imaging apparatuses 40c and 40d may perform an operation related to the probe 20 while communicating with a certain server. The probe 20 may be registered in the ultrasound imaging apparatuses 40c and 40d or may be registered in a certain server. The ultrasound imaging apparatuses 40c and 40d may communicate with the registered probe 20 and may perform an operation related to the probe 20.

The ultrasonic imaging apparatuses 40c and 40d may include various types of input/output interfaces such as a speaker, an LED, and a vibration device. For example, the ultrasonic imaging apparatuses 40c and 40d may output various pieces of information in the form of graphics, sound, or vibration through an input/output interface. The ultrasound imaging apparatuses 40c and 40d may output various notifications or data through input/output interfaces.

According to an embodiment, the ultrasound imaging apparatus 40a, 40b, 40c, or 40d may process an ultrasound images or obtain additional information from the ultrasound image, by using an artificial intelligence (AI) model. According to an embodiment, the ultrasound imaging apparatus 40a, 40b, 40c, or 40d may generate an ultrasound image or perform correction, image quality improvement, encoding, decoding, or the like on the ultrasound image, by using an AI model. According to an embodiment, the ultrasound imaging apparatus 40a, 40b, 40c, or 40d may perform baseline definition, anatomical information obtainment, lesion information obtainment, surface extraction, boundary definition, length measurement, area measurement, volume measurement, annotation creation, or the like from an ultrasound image, by using an AI model.

The AI model may be provided on the ultrasound imaging apparatus 40a, 40b, 40c, or 40d, or may be provided on a server.

The AI model may be implemented using various artificial neural network models or deep neural network models. The AI model may be trained and created using various machine learning algorithms or deep learning algorithms. The AI model may be implemented using a model such as a Convolutional Neural Network (CNN), a Recurrent Neural Network (RNN), a Generative Adversarial Network (GAN), or a Long Short-Term Memory (LSTM).

Figure 3:
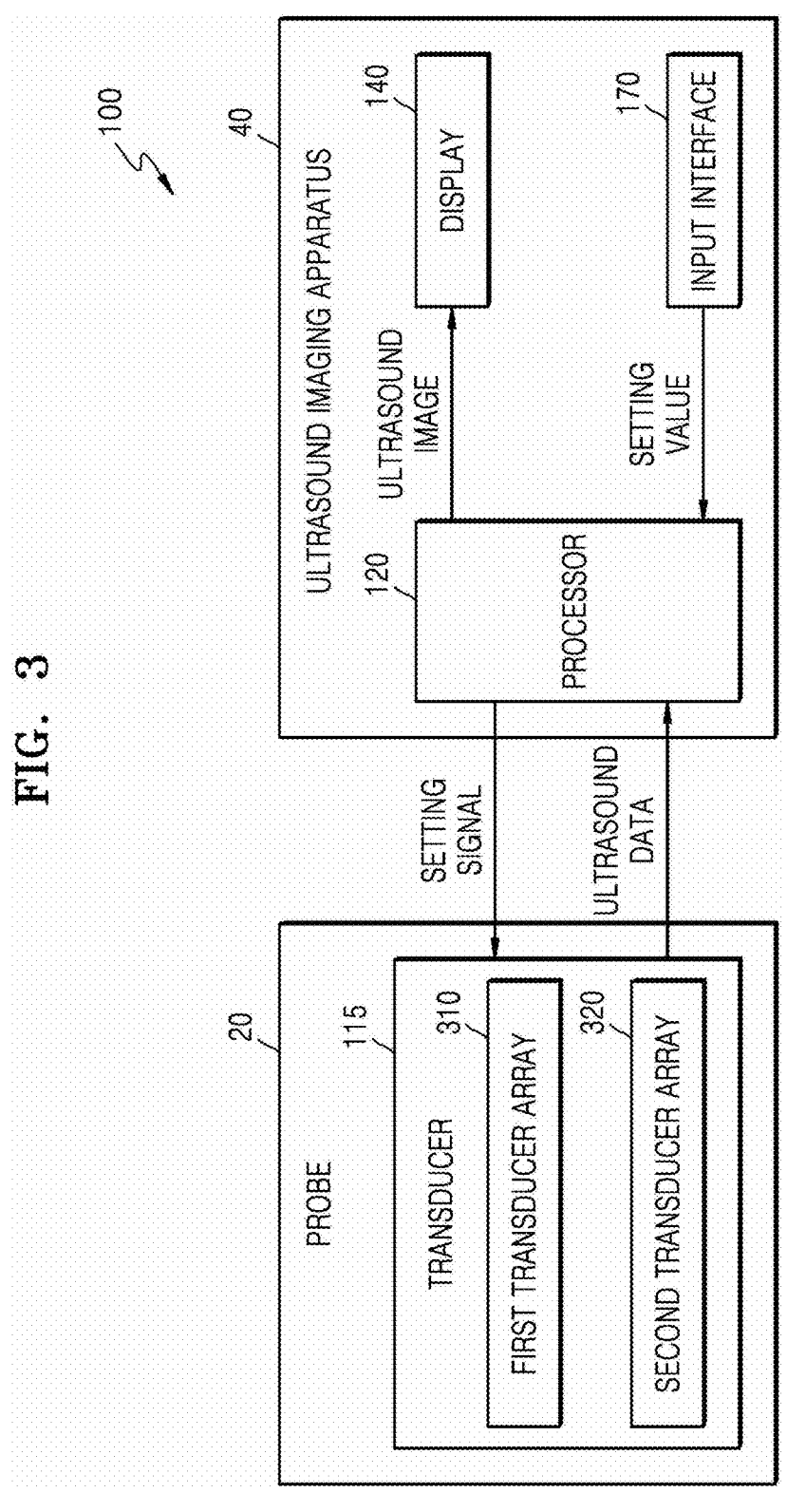
FIG. 3 is a block diagram of an ultrasound imaging system according to an embodiment.

FIG. 3 is a block diagram of the ultrasound imaging system 100 according to an embodiment. The ultrasound imaging system 100 according to an embodiment may include the probe 20 and the ultrasound imaging apparatus 40.

The probe 20 according to an embodiment may receive a setting signal from the ultrasound imaging apparatus 40. The setting signal may include a setting value for the ultrasound imaging apparatus 40 to display an ultrasound image. The probe 20 may transmit a transmission signal to an object, based on the setting signal. The probe 20 may generate ultrasound data by receiving an echo signal generated by reflecting the transmission signal. The probe 20 may transmit the ultrasound data to the ultrasound imaging apparatus 40.

The ultrasound imaging apparatus 40 according to an embodiment may receive a user input including the setting value. The ultrasound imaging apparatus 40 may transmit the setting value to the probe 20. The ultrasound imaging apparatus 40 may receive the ultrasound data from the probe 20. The ultrasound imaging apparatus 40 may display an ultrasound image based on the ultrasound data.

The probe 20 of the ultrasound imaging system 100 according to an embodiment may include the transducer 115. The transducer 115 may include a first transducer array 310 and a second transducer array 320. The ultrasound imaging apparatus 40 of the ultrasound imaging system 100 according to an embodiment may include an input interface 170, a processor 120, and a display 140.

The first transducer array 310 and the second transducer array 320 according to an embodiment may have different specifications. For example, the first transducer array 310 may be a convex transducer array, and the second transducer array 320 may be a linear transducer array. For example, the first transducer array 310 and the second transducer array 320 may have different transmission/reception frequencies.

The transducer 115 including the first transducer array 310 and the second transducer array 320 may receive the setting signal.

The transducer 115 according to an embodiment may select an activation transducer array used to generate an ultrasound image among the first transducer array 310 and the second transducer array 320, based on the setting signal. The transducer 115 may control the selected activation transducer array to transmit the transmission signal to the object. The transducer 115 may generate the ultrasound data by receiving an echo signal generated by reflecting the transmission signal. The transducer 115 may transmit the ultrasound data to the ultrasound imaging apparatus 40.

The input interface 170 according to an embodiment may receive the user input. The user input may be related to the setting value of the ultrasound image. For example, the user input may be an input for changing the setting value of the ultrasound image. The input interface 170 may transmit the setting value to the processor 120.

The processor 120 according to an embodiment may receive the setting signal from the input interface 170. The processor 120 may transmit the setting signal including the setting value to the transducer 115. The processor 120 may set an activation transducer array among the first transducer array 310 and the second transducer array 320, based on the setting value. The processor 120 may include a command of setting the activation transducer array, in the setting signal. The processor 120 may control the transducer 115 to generate the ultrasound data by using the activation transducer array. The processor 120 may receive the ultrasound data from the transducer 115. The processor 120 may generate the ultrasound image, based on the ultrasound data. The processor 120 may transmit the ultrasound image to the display 140.

The display 140 according to an embodiment may transmit the ultrasound image from the processor 120. The display 140 may display the ultrasound image.

FIG. 4 is a flowchart of a method of controlling the ultrasound imaging system 100, according to an embodiment.

In operation 410, the ultrasound imaging system 100 according to an embodiment may receive a user input related to the setting value of the ultrasound image. The ultrasound imaging system 100 may receive a user input of changing the setting value of the ultrasound image. For example, the ultrasound imaging system 100 may receive a zoom input of changing the magnification ratio of the ultrasound image. For example, the ultrasound imaging system 100 may receive a depth adjustment input of changing the depth of the ultrasound image.

In operation 420, the ultrasound imaging system 100 according to an embodiment may identify the setting value of the ultrasound image included in the user input. The ultrasound imaging system 100 may calculate a plurality of parameters that change in the ultrasound image, based on the setting value. For example, the ultrasound imaging system 100 may calculate a change in the magnification ratio of the ultrasound image from ×1 to ×4, based on the setting value. For example, the ultrasound imaging system 100 may calculate a change in the depth of the ultrasound image from 5 mm to 8 mm, based on the setting value.

In operation 430, the ultrasound imaging system 100 according to an embodiment may set an activation transducer array used to generate an ultrasound image among the first transducer array 310 and the second transducer array 320 having different specifications, based on the setting signal. The ultrasound imaging system 100 may set, as an activation transducer array, a transducer array that generates an ultrasound image to conform to the setting value among the first transducer array 310 and the second transducer array 320.

In operation 440, the ultrasound imaging system 100 according to an embodiment may receive ultrasound data through the activation transducer array. The ultrasound imaging system 100 may control the activation transducer array to transmit a transmission signal toward an object. The ultrasound imaging system 100 may receive an echo signal generated by reflecting the transmission signal. The ultrasound imaging system 100 may generate the ultrasound data, based on the echo signal. The ultrasound imaging system 100 may receive the generated ultrasound data.

In operation 450, the ultrasound imaging system 100 according to an embodiment may display the ultrasound image by using the ultrasound data. The ultrasound imaging system 100 may generate the ultrasound image, based on the ultrasound data. The ultrasound imaging system 100 may display the generated ultrasound image.

Figure 5:
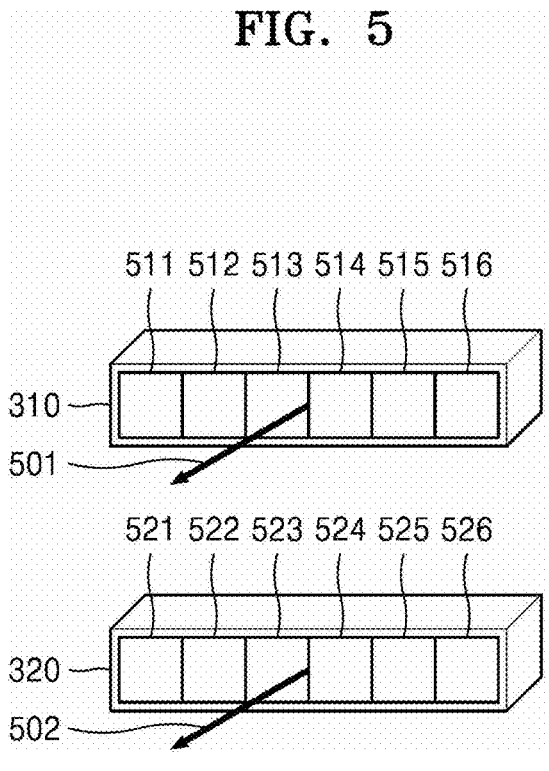
FIG. 5 illustrates a first transducer array and a second transducer array according to an embodiment.

FIG. 5 illustrates the first transducer array 310 and the second transducer array 320 according to an embodiment.

The first transducer array 310 and the second transducer array 320 may have central axes parallel to each other. A central axis may be located at the center of a transducer array, and may be perpendicular to a surface from which an ultrasonic signal is emitted. Respective central axes of a linear transducer array and a convex transducer array may be located at respective centers of the linear transducer array and the convex transducer array, and may be formed perpendicular to respective surfaces from which an ultrasonic signal is emitted. For example, the first transducer array 310 may have a first central axis 501. For example, the second transducer array 320 may have a second central axis 502.

The first central axis 501 and the second central axis 502 may be parallel to each other. When respective central axes of two transducer arrays are parallel to each other, the two transducer arrays may transmit transmission signals in the same directions. When respective central axes of two transducer arrays are parallel to each other, scan regions of the two transducer arrays may be directed in the same directions. In this case, there is no need to move a scan head of the probe 20 to search for the scan regions again, which may contribute to improving user convenience.

The probe 20 including the first transducer array 310 and the second transducer array 320 may be a single scan head type. The probe 20 of a single scan head type may have one scan head with a plurality of transducer arrays arranged side by side. The first transducer array 310 and the second transducer array 320 included in the probe 20 of a single scan head type may be arranged parallel to each other. For example, the first transducer array 310 and the second transducer array 320 may be arranged parallel to each other in a lateral direction. For example, the first transducer array 310 and the second transducer array 320 may be arranged parallel to each other in a vertical direction.

The first transducer array 310 according to an embodiment may include a plurality of transducer units 511, 512, 513, 514, 515, and 516 arranged in an array structure. For example, the first transducer array 310 may include a first transducer unit 511, a second transducer unit 512, a third transducer unit 513, a fourth transducer unit 514, a fifth transducer unit 515, and a sixth transducer unit 516. The plurality of transducer units 511, 512, 513, 514, 515, and 516 may be arranged in a row.

The second transducer array 320 according to an embodiment may include a plurality of transducer units 521, 522,

523, 524, 525, and 526 arranged in an array structure. For example, the second transducer array 320 may include a first transducer unit 521, a second transducer unit 522, a third transducer unit 523, a fourth transducer unit 524, a fifth transducer unit 525, and a sixth transducer unit 526. The plurality of transducer units 521, 522, 523, 524, 525, and 526 may be arranged in a row.

The first transducer array 310 and the second transducer array 320 according to an embodiment may have different specifications. For example, the first transducer array 310 and the second transducer array 320 may transmit and receive frequency components belonging to different frequency bands. The first transducer array 310 may have a first structure among a plurality of structures, and the second transducer array 320 may have a second structure among a plurality of structures.

The first transducer array 310 and the second transducer array 320 may be piezoelectric bodies that generate ultrasonic waves by converting electrical energy into mechanical vibration. However, embodiments are not limited thereto, and the first transducer array 310 and the second transducer array 320 may have a semiconductor structure. The semiconductor structure may include a single structure or may include multiple structures which are continuously coupled without separation. The first transducer array 310 and the second transducer array 320 may be implemented according to a cMUT or pMUT method. The plurality of structures that the first transducer array 310 and the second transducer array 320 may have may include a lead zirconate titanate (PZT)-based piezoelectric structure, a single crystal-based piezoelectric structure, a polymer-based piezoelectric structure, a structure using a piezoelectric composite, a capacitive micromachined ultrasonic transducer (cMUT) structure using micro-electromagnetic system (MEMS) technology, and a piezoelectric micromachined ultrasonic transducer (pMUT) structure using MEMS technology.

Figure 6A:
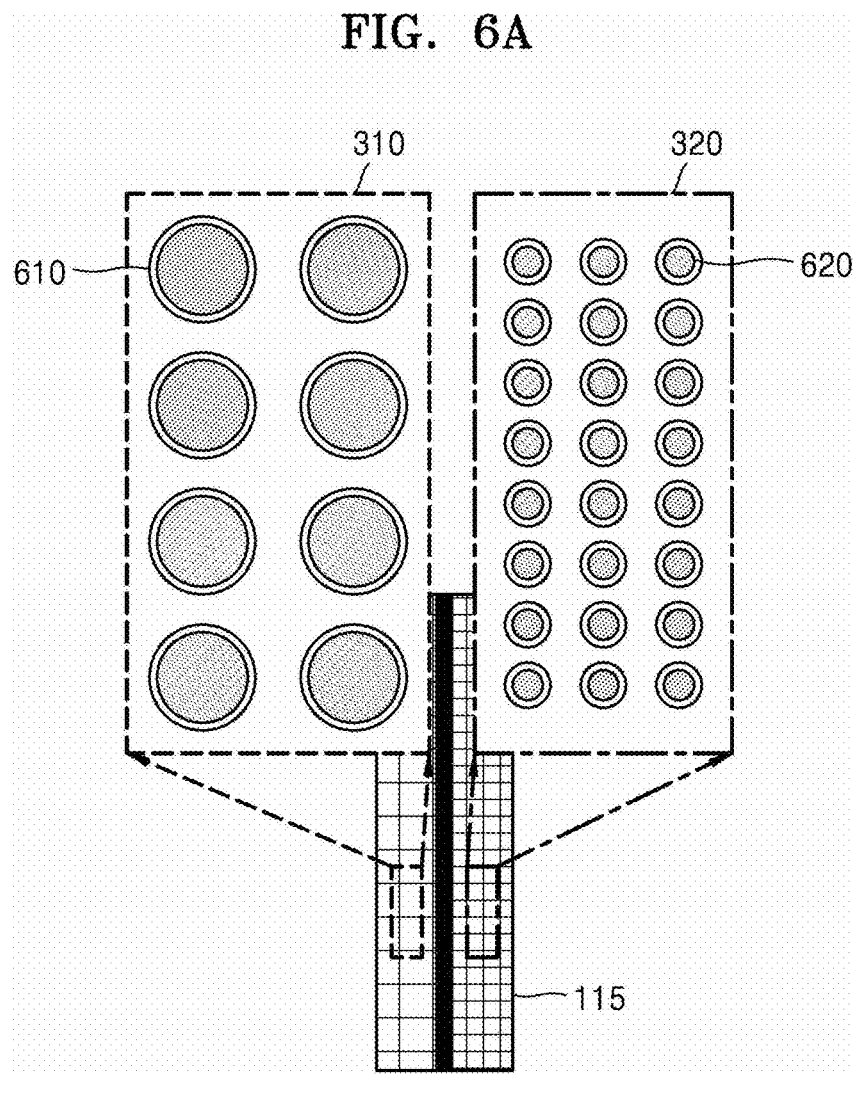
FIG. 6A illustrates first transducer units included in a first transducer array and second transducer units included in a second transducer array, according to an embodiment.

FIG. 6A illustrates first transducer units 610 included in the first transducer array 310 and second transducer units 620 included in the second transducer array 320, according to an embodiment.

The transducer 115 according to an embodiment may include the first transducer array 310 and the second transducer array 320. The first transducer array 310 and the second transducer array 320 may be arranged to be directed in the same directions. The first transducer array 310 and the second transducer array 320 may transmit transmission signals in the same directions.

The first transducer array 310 according to an embodiment may include a plurality of first transducer units 610. Each of the plurality of first transducer units 610 may have a first size. The first transducer array 310 may transmit and receive a signal in a first frequency band.

The second transducer array 320 according to an embodiment may include a plurality of second transducer units 620. Each of the plurality of second transducer units 620 may have a second size. The second transducer array 320 may transmit and receive a signal in a second frequency band.

The first transducer array 310 and the second transducer array 320 according to an embodiment may each have a next-generation xMUT probe structure. The first transducer array 310 and the second transducer array 320 may each have a multi-cell structure.

Figure 6B:
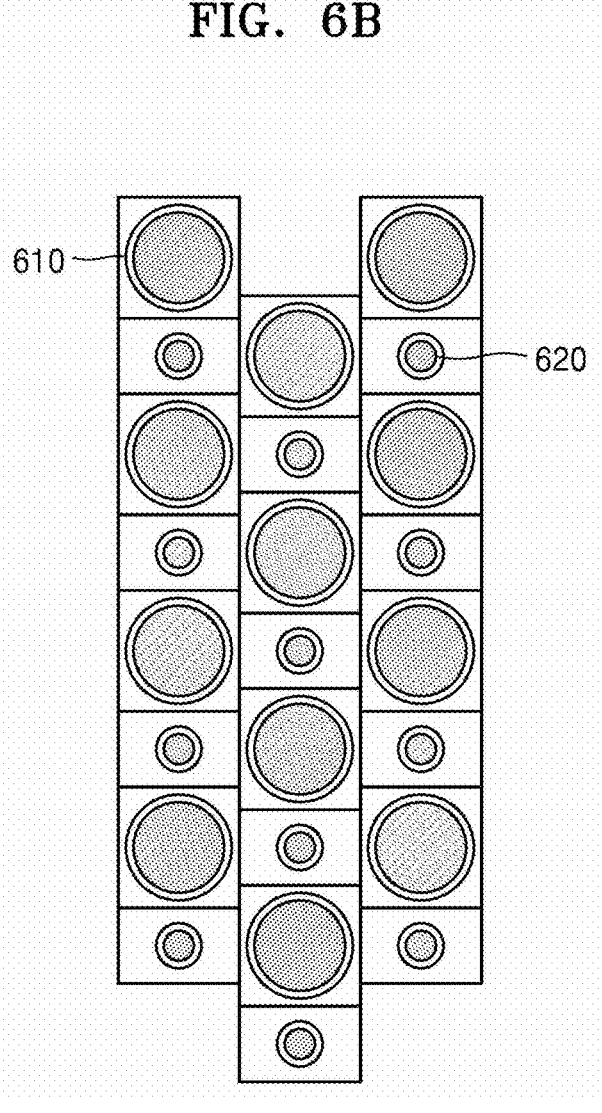
FIG. 6B illustrates a plurality of transducer units according to an embodiment.

FIG. 6B illustrates a plurality of transducer units 610 and 620 according to an embodiment.

The transducer 115 according to an embodiment may include a plurality of transducer units 610 and 620 having different specifications. For example, the transducer 115 may include a plurality of first transducer units 610 having a first specification and a plurality of second transducer units 620 having a second specification. The plurality of first transducer units 610 may transmit and receive a signal in a first frequency band. The plurality of second transducer units 620 may transmit and receive a signal in a second frequency band. The plurality of first transducer units 610 and the plurality of second transducer units 620 may be arranged alternately in a plan view. For example, the plurality of first transducer units 610 and the plurality of second transducer units 620 may be arranged in a zigzag structure.

The plurality of first transducer units 610 and the plurality of second transducer units 620 according to an embodiment may each have a next-generation xMUT probe structure. The plurality of first transducer units 610 and the plurality of second transducer units 620 may each have a multi-cell structure.

The transducer 115 of the probe 20 according to the disclosure may have a structure in which the first transducer array 310 and the second transducer array 320 are distinguished from each other as shown in FIG. 6A, or an array structure in which a plurality of transducer units 610 and 620 are arranged without distinction between the first transducer array 310 and the second transducer array 320 as shown in FIG. 6B. The probe 20 according to the disclosure may include a plurality of transducer arrays 310 and 320 including a plurality of transducer units 610 and 620 in a light, thin, simple, and small shape. Accordingly, in the probe 20 according to the disclosure, a plurality of transducer units 610 and 620 having different specifications may be easily realized on one scan head.

Figure 7:
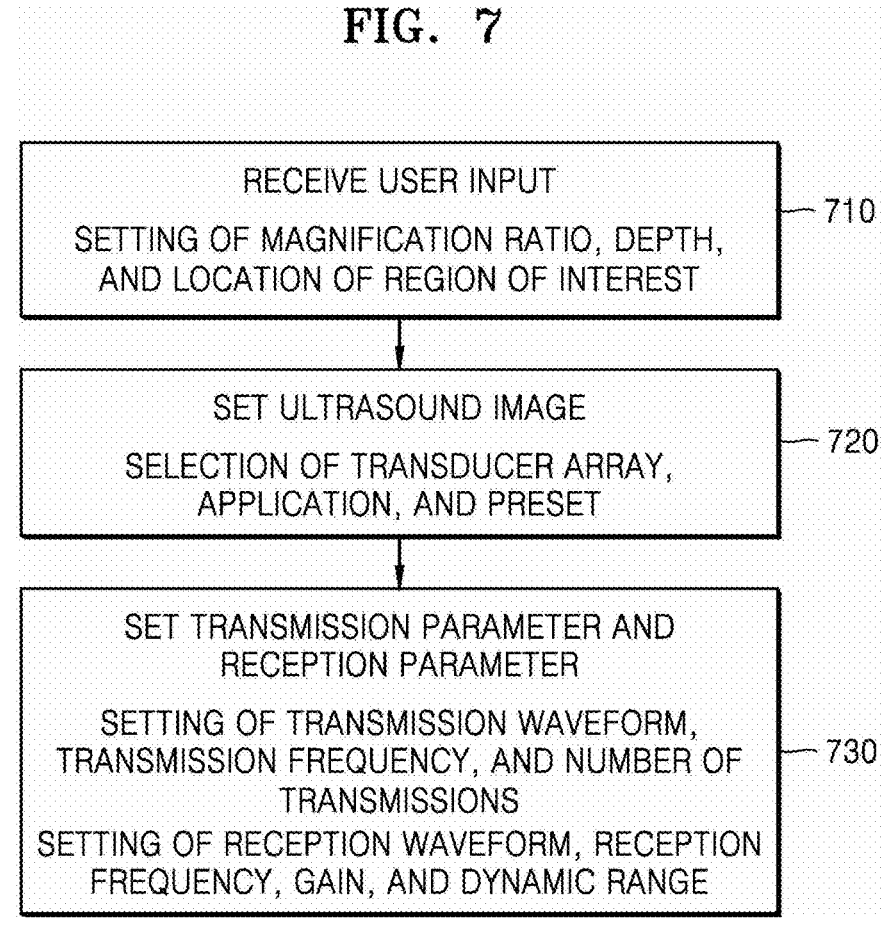
FIG. 7 is a flowchart illustrating an ultrasound imaging system, according to an embodiment, setting an activation transducer array and setting transmission parameters and reception parameters.

FIG. 7 is a flowchart illustrating an ultrasound imaging system according to an embodiment setting an activation transducer array and setting transmission parameters and reception parameters.

In operation 710, the ultrasound imaging system 100 according to an embodiment may receive a user input. Examples of the user input may include an input of activating a zoom function, an input of adjusting a zoom ratio, and an input of varying an imaging depth. The user input may include a setting value related to an ultrasound image. For example, the setting value may include at least one of the magnification ratio of the ultrasound image, the depth of the ultrasound image, and the location of a region of interest of the ultrasound image. The magnification ratio of the ultrasound image may be a ratio for zooming the ultrasound image compared to a basic ratio. The depth of the ultrasound image may be a penetration depth which is identifiable in the ultrasound image. The region of interest of the ultrasound image may be a region of the ultrasound image that a user intends to analyze precisely. The ultrasound imaging system 100 may identify the setting value included in the user input. The ultrasound imaging system 100 may set the magnification ratio of the ultrasound image, the depth of the ultrasound image, and the location of the region of interest of the ultrasound image, based on the setting value.

In operation 720, the ultrasound imaging system 100 according to an embodiment may set an ultrasound image. The ultrasound imaging system 100 may set an ultrasound image that is to be displayed, based on the setting value. The ultrasound imaging system 100 may select a transducer array for transmitting a transmission signal in order to obtain the set ultrasound image. For example, the ultrasound imaging system 100 may select an activation transducer array for obtaining an ultrasound image from among a plurality of transducer arrays. In order to obtain the set ultrasound image, the ultrasound imaging system 100 may select an application for obtaining ultrasound data and generating an ultrasound image. The ultrasound imaging system 100 may select a preset for obtaining the set ultrasound image.

The ultrasound imaging system 100 according to an embodiment may perform basic image setting. The ultrasound imaging system 100 may automatically change the activation transducer array by analyzing image performance changed by user manipulation.

In operation 730, the ultrasound imaging system 100 according to an embodiment may set a transmission parameter and a reception parameter. The transmission parameter may be a parameter related to a transmission signal transmitted by the ultrasound imaging system 100. For example, the transmission parameter may include at least one of a transmission waveform, a transmission frequency, and the number of transmissions. The reception parameter may be a parameter related to an echo signal received by the ultrasound imaging system 100. For example, the reception parameter may include at least one of a reception waveform, a reception frequency, a gain, and a dynamic range.

The ultrasound imaging system 100 according to an embodiment may set the transmission parameter and the reception parameter such that the degree of change in the ultrasound image may be maintained within a critical range before and after the activation transducer array is changed. The ultrasound imaging system 100 may display the ultrasound image by automatically optimizing the transmission parameter and reception parameter of the activation transducer array by feeding the basic image setting back. Accordingly, the ultrasound imaging system 100 according to the disclosure may improve the user's manipulation convenience for displaying the ultrasound image corresponding to the setting value and improve the performance of the ultrasound image that is to be displayed.

The ultrasound imaging system 100 according to an embodiment may set the transmission parameter and the reception parameter by using at least one of the correlation coefficient of the ultrasound image, the bias value of the ultrasound image, and artificial intelligence that analyzes the ultrasound image, before and after the activation transducer array is changed. For example, when an ultrasound image type, a transmission/reception frequency, or a preset change occurs due to a change in the activation transducer array or a change in an application being used, the ultrasound imaging system 100 according to an embodiment may provide an optimized ultrasound image by adding previous ultrasound image setting information to preset information included in the ultrasound image after the change.

Figure 8:
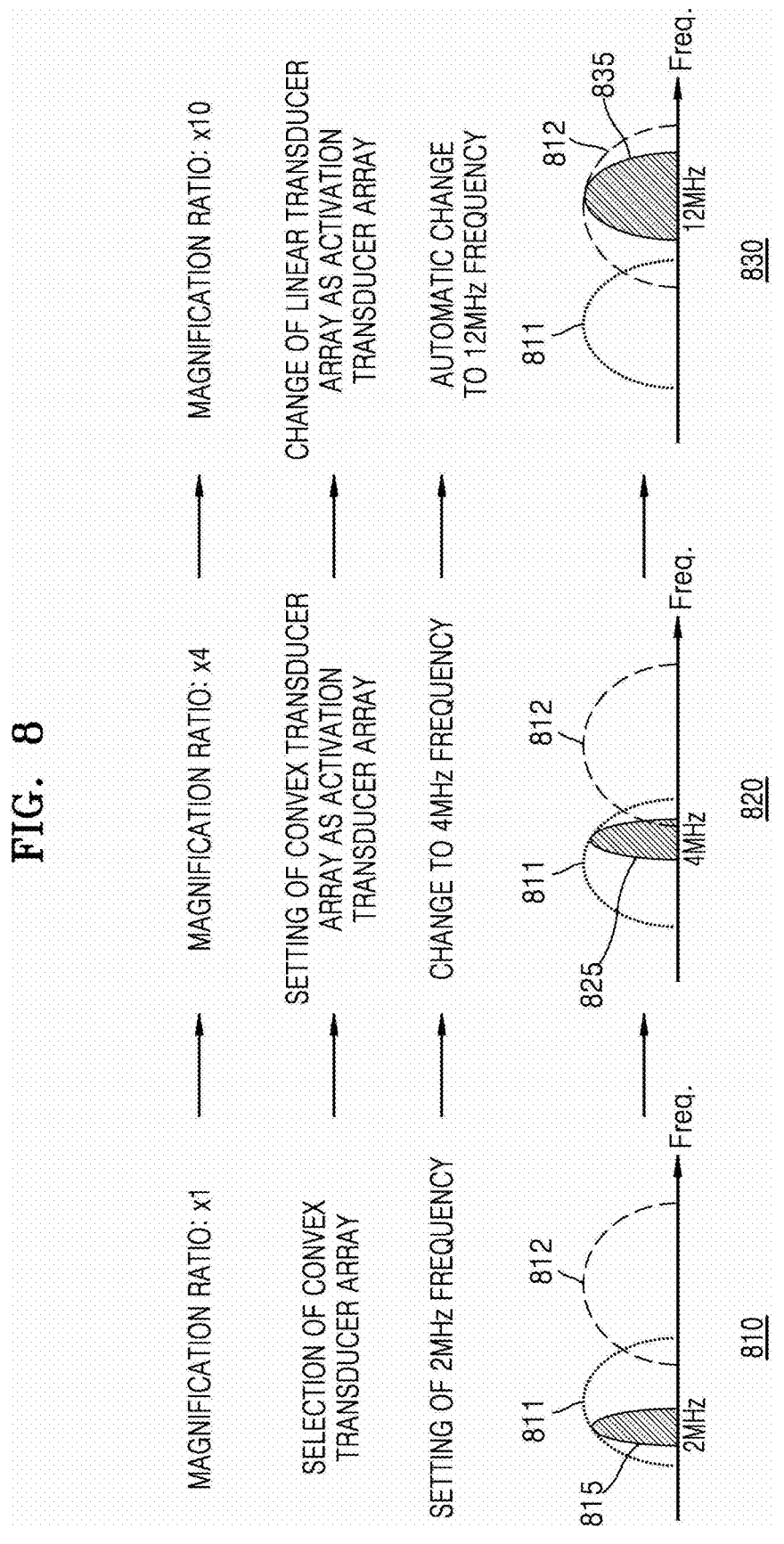
FIG. 8 is a diagram illustrating an ultrasound imaging system, according to an embodiment, setting a frequency spectrum or an activation transducer array when changing the magnification ratio of an ultrasound image.

FIG. 8 is a diagram illustrating the ultrasound imaging system 100 according to an embodiment setting a frequency spectrum or an activation transducer array when changing the magnification ratio of an ultrasound image.

In situation 810, the ultrasound imaging system 100 according to an embodiment may set the magnification ratio to be ×1. The setting of the magnification ratio to be ×1 may be referred to as setting a default magnification ratio. The ultrasound imaging system 100 may display the ultrasound image set with the default magnification ratio.

The ultrasound imaging system 100 may select a convex transducer array to display the ultrasound image set with the default magnification ratio. The convex transducer array may correspond to the first transducer array 310 described above with reference to FIG. 3. The convex transducer array may transmit and receive an ultrasonic signal belonging to a first frequency band 811.

The ultrasound imaging system 100 may set the transmission/reception frequency as a first frequency spectrum 815 to display the ultrasound image set with the default magnification ratio. For example, the ultrasound imaging system 100 may set the transmission/reception frequency as 2 MHz belonging to the first frequency spectrum 811 in order to display the ultrasound image set with the default magnification ratio. When the ultrasound imaging system 100 displays the ultrasound image set with the default magnification ratio, a transducer array using a second frequency band 812 may be deactivated.

In situation 820, the ultrasound imaging system 100 according to an embodiment may set the magnification ratio to be ×4. The ultrasound imaging system 100 may receive a user input for changing an ultrasound image set at a default magnification ratio to a first magnified ultrasound image having a magnification ratio of ×4. For example, the ultrasound imaging system 100 may receive a user's zoom input of changing the ultrasound image to the first magnified ultrasound image. For example, the ultrasound imaging system 100 may receive a button input indicating a ×4 magnification ratio in numbers or a drag input using a pointer such as a finger.

The ultrasound imaging system 100 may set a convex transducer array as the activation transducer array to display the first magnified ultrasound image. The activation transducer array may be a transducer array used to display an ultrasound image. The activation transducer array may be a transducer array for transmitting a transmission signal to display an ultrasound image. The convex transducer array may transmit and receive an ultrasonic signal belonging to the first frequency band 811.

The ultrasound imaging system 100 may set the transmission/reception frequency as a second frequency spectrum 825 to display the first magnified ultrasound image. For example, the ultrasound imaging system 100 may set the transmission/reception frequency as 4 MHz to display the first magnified ultrasound image. 4 MHz may belong to the first frequency band 811. The ultrasound imaging system 100 may change the spectrum of the transmission/reception frequency within the first frequency band 811 from the first frequency spectrum 815 to the second frequency spectrum 825. When the ultrasound imaging system 100 displays the first magnified ultrasound image, a transducer array using the second frequency band 812 may be deactivated.

When the magnification ratio is no less than a minimum change value and less than a first threshold value, the ultrasound imaging system 100 may change the transmission/reception frequency of the activation transducer array. The minimum change value may be a magnification ratio that causes the transmission/reception frequency of the activation transducer array to change. For example, the minimum change value may be ×1. The first threshold value may be a maximum magnification ratio capable of changing the transmission/reception frequency without changing the activation transducer array. For example, the first threshold value may be ×5.

In situation 830, the ultrasound imaging system 100 according to an embodiment may set the magnification ratio to be ×10. The ultrasound imaging system 100 may receive a user input for changing the first magnified ultrasound image to a second magnified ultrasound image having a magnification ratio of ×10. For example, the ultrasound imaging system 100 may receive a user's zoom input of changing the first magnified ultrasound image to the second magnified ultrasound image. For example, the ultrasound imaging system 100 may receive a button input indicating a ×10 magnification ratio in numbers or a drag input using a pointer such as a finger.

The ultrasound imaging system 100 may change the activation transducer array from the convex transducer array to the linear transducer array to display the second magnified ultrasound image. The linear transducer array may transmit and receive an ultrasonic signal belonging to the second frequency band 812. The second frequency band 812 may be higher than the first frequency band 811.

The ultrasound imaging system 100 may set the transmission/reception frequency as a third frequency spectrum 835 to display the second magnified ultrasound image. For example, the ultrasound imaging system 100 may set the transmission/reception frequency as 12 MHz to display the second magnified ultrasound image. 12 MHz may belong to the second frequency band 812. The ultrasound imaging system 100 may automatically change the transmission/reception frequency to 12 MHz belonging to the second frequency band 812. The ultrasound imaging system 100 may automatically change the activation transducer array from the convex transducer array to the linear transducer array. When the ultrasound imaging system 100 displays the second magnified ultrasound image, a convex transducer array using the first frequency band 811 may be deactivated.

When the magnification ratio is no less than the first threshold value, the ultrasound imaging system 100 may change the activation transducer array. When using a zoom function of magnifying an ultrasound image, the ultrasound imaging system 100 may set a transducer array capable of automatically providing an ultrasound area with a high resolution as the activation transducer array when having a magnification ratio equal to or greater than the first threshold value. For example, when the first threshold value is ×5, the ultrasound imaging system 100 may automatically change the activation transducer array from the convex transducer array to the linear transducer array when the magnification ratio is ×5 or greater. Accordingly, the ultrasound imaging system 100 according to the disclosure may improve the performance of displaying a magnified ultrasound image, by automatically changing the activation transducer array in response to a user input of changing the magnification ratio of an ultrasound image.

Figure 9:
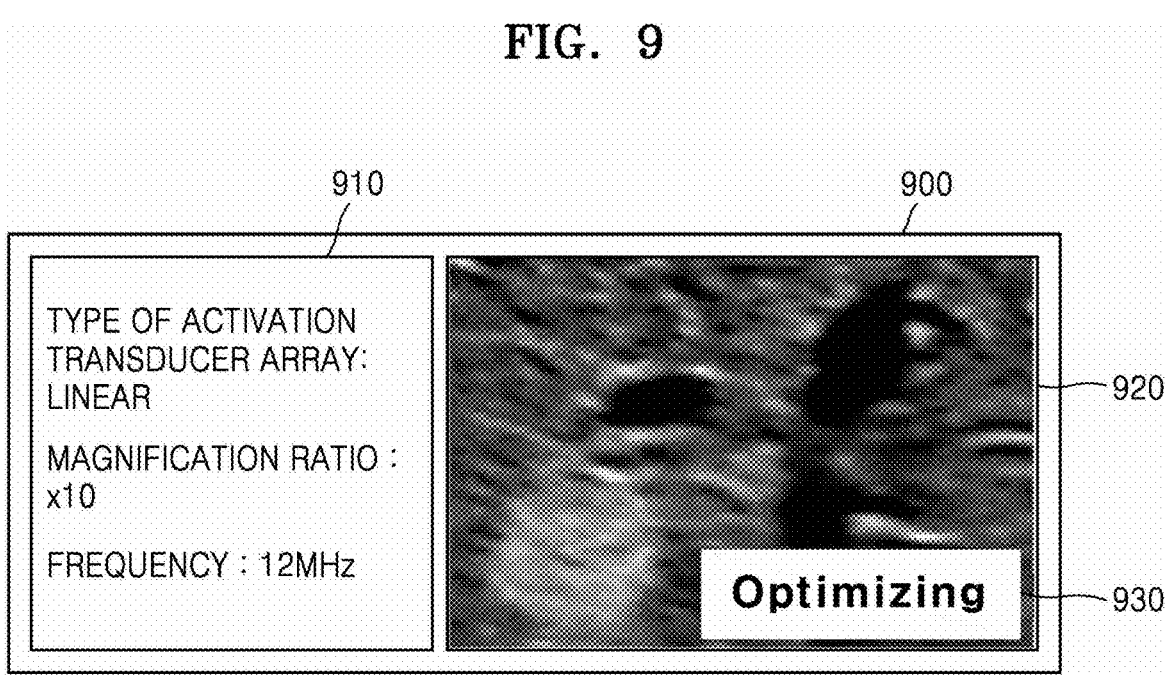
FIG. 9 is a first user interface displayed when an ultrasound imaging system, according to an embodiment, changes the magnification ratio of an ultrasound image.

FIG. 9 is a first UI 900 displayed when the ultrasound imaging system 100 according to an embodiment changes the magnification ratio of an ultrasound image. The ultrasound imaging system 100 may display the first UI 900 via the display 140 of the ultrasound imaging apparatus 40. The first UI 900 may include an information display area 910, an image display area 920, and a guidance window 930.

The information display area 910 may display information about an activation transducer. For example, the information display area 910 may display text indicating that the type of an activation transducer array is linear. The information display area 910 may display information regarding driving conditions of the activation transducer. For example, the information display area 910 may display text indicating that the magnification ratio is ×10. For example, the information display area 910 may display text indicating that a frequency used for transmission/reception by the activation transducer is 12 MHz.

The image display area 920 may display an ultrasound image. The image display area 920 may display an ultrasound image obtained using the activation transducer displayed on the information display area 910. The image display area 920 may display an ultrasound image obtained under the driving conditions displayed on the information display area 910. For example, the image display area 920 may display an ultrasound image obtained by magnifying a part of an object 10 times compared to a basic ultrasound image.

The guidance window 930 may be a window notifying that a function for setting the activation transducer array has been executed. The guidance window 930 may be formed to overlap the image display area 920. For example, the guidance window 930 may be formed in a right lower portion of the image display area 920. The guidance window 930 may provide information indicating that the activation transducer array is automatically selected based on the setting value of the ultrasound image. For example, the guidance window 930 may display a guiding phrase "Optimizing." Thus, a user may know that the ultrasound imaging system 100 is automatically selecting the activation transducer array, based on the setting value of the ultrasound image.

The ultrasound imaging system 100 may terminate a function of setting the activation transducer array, in response to a function termination input received through a guidance window. For example, the ultrasound imaging system 100 may terminate a function of setting the activation transducer array, in response to an input of clicking a guidance window. Accordingly, when the user does not wish for the ultrasound imaging system 100 to automatically select the activation transducer array, the user may conveniently terminate the function of setting the activation transducer array.

Figure 10:
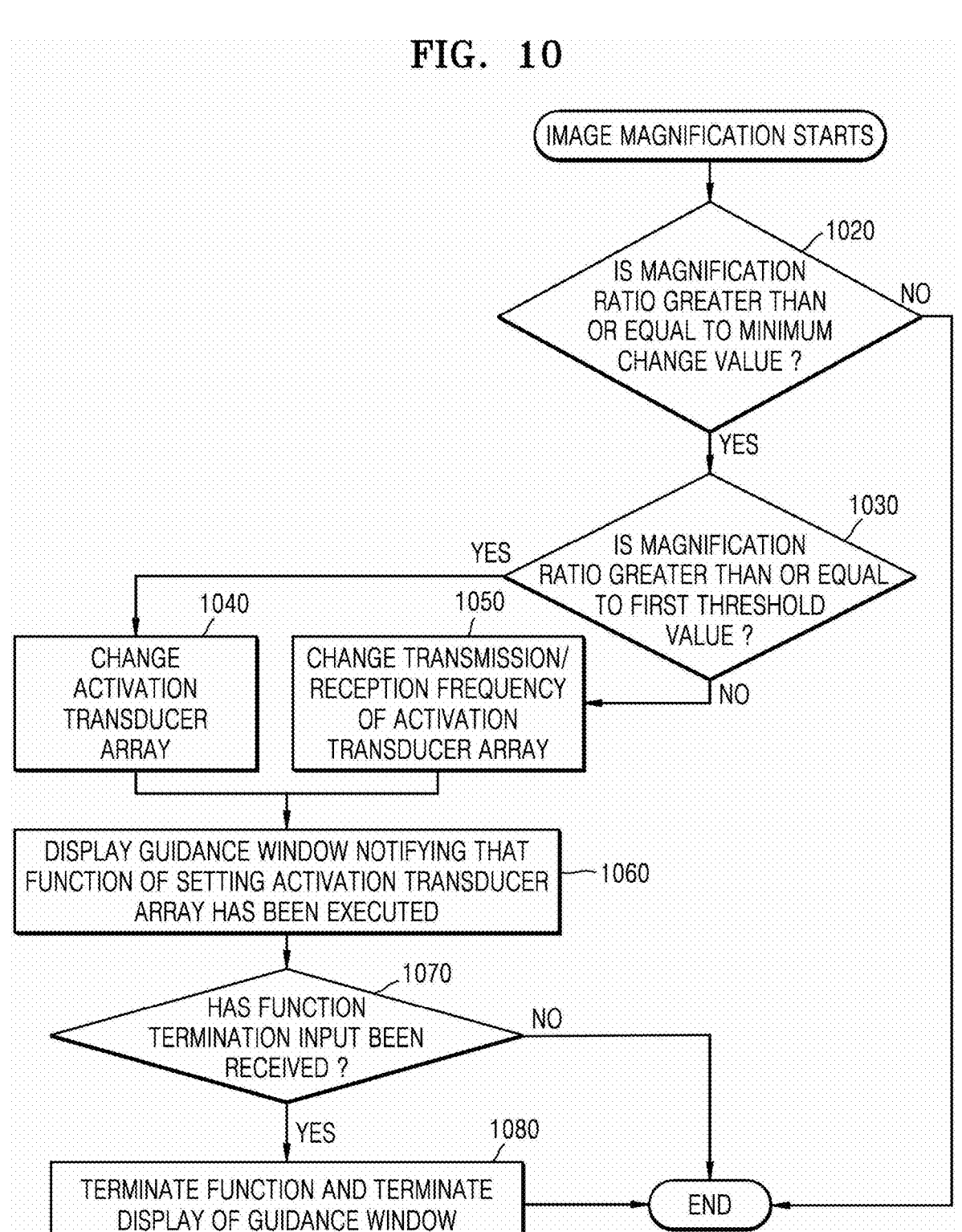
FIG. 10 is a flowchart of a process, performed by an ultrasound imaging system according to an embodiment, of setting a frequency spectrum or an activation transducer array when changing the magnification ratio of an ultrasound image.

FIG. 10 is a flowchart of a process, performed by the ultrasound imaging system 100 according to an embodiment, of setting a frequency spectrum or an activation transducer array when changing the magnification ratio of an ultrasound image. FIG. 10 may begin in a situation when the ultrasound imaging system 100 receives a user input of magnifying an ultrasound image.

In operation 1020, the ultrasound imaging system 100 according to an embodiment may identify whether the magnification ratio is greater than or equal to a minimum change value. The minimum change value may be a magnification ratio that causes the transmission/reception frequency of the activation transducer array to change. For example, the minimum change value may be ×1. The ultrasound imaging system 100 may proceed to operation 1030 when the magnification ratio is greater than or equal to the minimum change value (operation 1020—YES). When the magnification ratio is less than the minimum change value (operation 1020—NO), the ultrasound imaging system 100 may terminate the process of setting an activation transducer array.

In operation 1030, the ultrasound imaging system 100 according to an embodiment may identify whether the magnification ratio is greater than or equal to a first threshold value. The first threshold value may be a maximum magnification ratio capable of changing the transmission/reception frequency without changing the activation transducer array. For example, the first threshold value may be ×5. The ultrasound imaging system 100 may proceed to operation 1040 when the magnification ratio is greater than or equal to the minimum change value (operation 1030—YES). The ultrasound imaging system 100 may proceed to operation 1050 when the magnification ratio is greater than or equal to the first threshold value (operation 1030—NO).

In operation 1040, the ultrasound imaging system 100 according to an embodiment may change the activation transducer array. The activation transducer array may be a transducer array used by the ultrasound imaging system 100 to obtain an ultrasound image. When the magnification ratio is no less than the first threshold value, the ultrasound imaging system 100 may automatically change the activation transducer array. For example, when the magnification ratio is ×10, the ultrasound imaging system 100 may change the activation transducer array from the convex transducer array to the linear transducer array.

In operation 1050, the ultrasound imaging system 100 according to an embodiment may change the transmission/reception frequency of the activation transducer array. When the magnification ratio is no less than the minimum change value and less than the first threshold value, the ultrasound imaging system 100 may change the transmission/reception frequency of the activation transducer array while maintaining the activation transducer array. For example, when the magnification ratio is ×4, the ultrasound imaging system 100 may change the transmission/reception frequency of the activation transducer array to 4 MHz while maintaining the convex transducer array as the activation transducer array.

In operation 1060, the ultrasound imaging system 100 according to an embodiment may display a guidance window notifying that a function of setting an activation transducer array has been executed. The ultrasound imaging system 100 may provide information that a function of automatically selecting an activation transducer array is being executed, through the guidance window. For example, the ultrasound imaging system 100 may display a guiding phrase "Optimizing" through the guidance window.

In operation 1070, the ultrasound imaging system 100 according to an embodiment may identify whether a function termination input has been received. The ultrasound imaging system 100 may identify whether a function termination input has been received, through the information window. For example, the ultrasound imaging system 100 may identify whether an input of clicking the information window has been received. The ultrasound imaging system 100 may proceed to operation 1080 when the function termination input has been received (operation 1070—YES). When the function termination input has not been received (operation 1070—NO), the ultrasound imaging system 100 may maintain a state of continuously executing the function of setting the activation transducer array.

In operation 1080, the ultrasound imaging system 100 according to an embodiment may terminate the function of setting the activation transducer array. The ultrasound imaging system 100 may terminate the function of setting the activation transducer array, in response to the function termination input. The ultrasound imaging system 100 may terminate display of the guidance window notifying that the function of setting an activation transducer array has been executed.

FIG. 11 is a diagram illustrating the ultrasound imaging system 100 according to an embodiment setting a frequency spectrum or an activation transducer array when changing the depth of an ultrasound image.

In situation 1110, the ultrasound imaging system 100 according to an embodiment may set the depth of the ultrasound image to be 5 mm. The setting of the depth of the ultrasound image to be 5 mm may be referred to as setting a basic depth. The ultrasound imaging system 100 may display the ultrasound image representing an object by the basic depth.

The ultrasound imaging system 100 may select a linear transducer array to display the ultrasound image representing an object by the basic depth. The linear transducer array may correspond to the second transducer array 320 described above with reference to FIG. 3. The linear transducer array may transmit and receive an ultrasonic signal belonging to a second frequency band 1102.

The ultrasound imaging system 100 may set the transmission/reception frequency as a first frequency spectrum 1105 to display the ultrasound image representing an object by the basic depth. For example, the ultrasound imaging system 100 may set the transmission/reception frequency as 12 MHz belonging to the second frequency spectrum 1102 in order to display the ultrasound image representing an object by the basic depth. When the ultrasound imaging system 100 displays the ultrasound image representing an object by the basic depth, a transducer array using a first frequency band 1101 may be deactivated.

In situation 1120, the ultrasound imaging system 100 according to an embodiment may set the depth of the ultrasound image to be 8 mm. The ultrasound imaging system 100 may receive a user input for changing the ultrasound image to a first depth ultrasound image capable of representing the object with a depth greater than the basic depth. For example, the ultrasound imaging system 100 may receive a user's depth increasing input of changing the ultrasound image to the first depth ultrasound image. For example, the ultrasound imaging system 100 may receive a button input indicating the depth of 8 mm as a number.

The ultrasound imaging system 100 may set a linear transducer array as the activation transducer array to display the first depth ultrasound image. The activation transducer array may be a transducer array used to display an ultrasound image. The activation transducer array may be a transducer array for transmitting a transmission signal to display an ultrasound image. The linear transducer array may transmit and receive an ultrasonic signal belonging to the second frequency band 1102.

The ultrasound imaging system 100 may set the transmission/reception frequency as a second frequency spectrum 1125 to display the first depth ultrasound image. For example, the ultrasound imaging system 100 may set the transmission/reception frequency as 6 MHz to display the first depth ultrasound image. 6 MHz may belong to the second frequency band 1102. The ultrasound imaging system 100 may change the spectrum of the transmission/reception frequency within the second frequency band 1102 from the first frequency spectrum 1105 to the second frequency spectrum 1125. When the ultrasound imaging system 100 displays the first depth ultrasound image, a transducer array using the first frequency band 1101 may be deactivated.

When a signal magnitude at a maximum depth within the ultrasound image is greater than or equal to a minimum identification value, the ultrasound imaging system 100 may change the transmission/reception frequency of the activation transducer array. The minimum identification value may be a minimum value capable of identifying an ultrasound image generated using a signal. For example, the minimum identification value may be −20 dB.

In situation 1130, the ultrasound imaging system 100 according to an embodiment may set the depth of the ultrasound image to be 12 mm. The ultrasound imaging system 100 may receive a user input for changing the ultrasound image to a second depth ultrasound image capable of representing the object with a greater depth than the first depth ultrasound image. For example, the ultrasound imaging system 100 may receive a user's depth increasing input of changing the first depth ultrasound image to the second depth ultrasound image. For example, the ultrasound imaging system 100 may receive a button input indicating the depth of 12 mm as a number.

The ultrasound imaging system 100 may change the activation transducer array from the linear transducer array to the convex transducer array to display the second depth ultrasound image. The convex transducer array may transmit and receive an ultrasonic signal belonging to the first frequency band 1101. The first frequency band 1101 may be lower than the second frequency band 1102.

The ultrasound imaging system 100 may set the transmission/reception frequency as a third frequency spectrum 1135 to display the second depth ultrasound image. For example, the ultrasound imaging system 100 may set the transmission/reception frequency as 4 MHz to display the second depth ultrasound image. 4 MHz may belong to the first frequency band 1101. The ultrasound imaging system 100 may automatically change the transmission/reception frequency to 4 MHz belonging to the first frequency band 1101. The ultrasound imaging system 100 may automatically change the activation transducer array from the linear transducer array to the convex transducer array. When the ultrasound imaging system 100 displays the second depth ultrasound image, a linear transducer array using the second frequency band 1102 may be deactivated.

When the ultrasound imaging system 100 is unable to change the transmission/reception frequency of a current activation transducer array, the ultrasound imaging system 100 may change the current activation transducer array. For example, when the ultrasound imaging system 100 is unable to change the transmission/reception frequency of a linear activation transducer array that is a current activation transducer array, the ultrasound imaging system 100 may automatically change the current activation transducer array from the linear transducer array to the convex transducer array. Accordingly, the ultrasound imaging system 100 according to the disclosure may improve the performance of displaying an ultrasound image having a changed depth, by automatically changing the activation transducer array in response to a user input of changing the depth of an ultrasound image.

Figure 12:
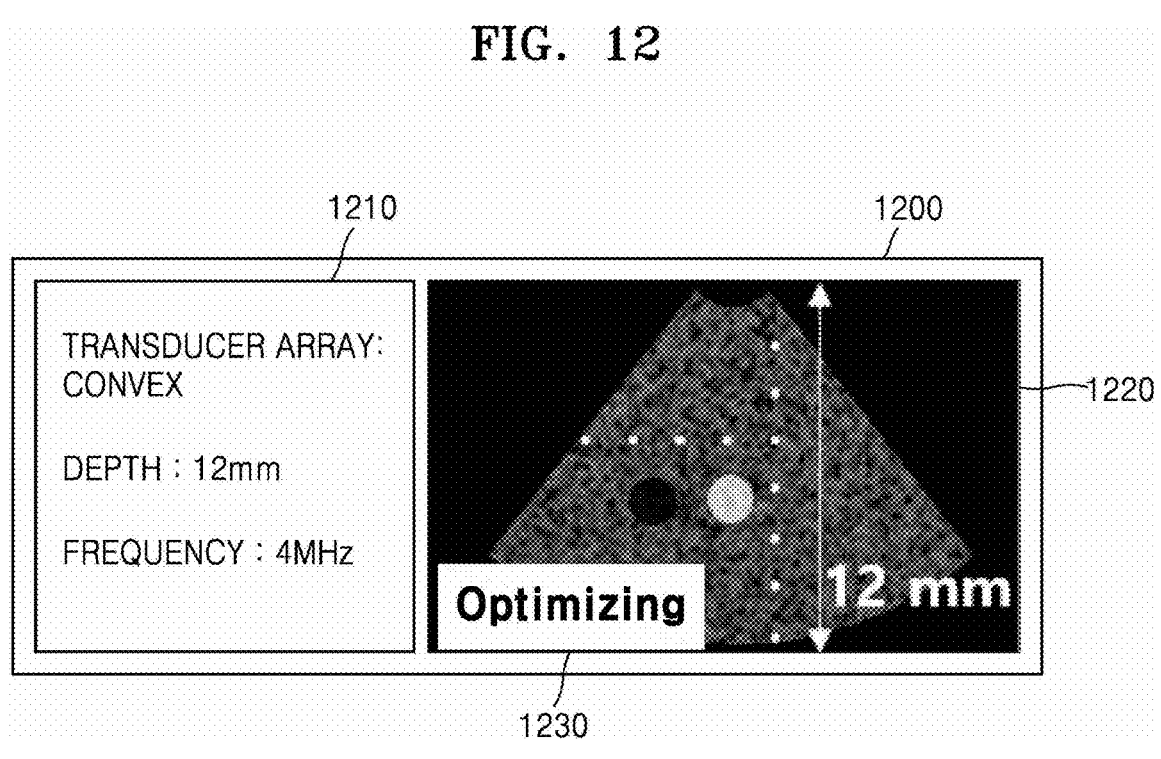
FIG. 12 is a second user interface displayed when an ultrasound imaging system, according to an embodiment, changes the depth of an ultrasound image.

FIG. 12 is a second UI 1200 displayed when the ultrasound imaging system 100 according to an embodiment changes the depth of an ultrasound image. The ultrasound imaging system 100 may display the second UI 1200 via the display 140 of the ultrasound imaging apparatus 40. The second UI 1200 may include an information display area 1210, an image display area 1220, and a guidance window 1230.

The information display area 1210 may display information about an activation transducer. For example, the information display area 1210 may display text indicating that the type of an activation transducer array is convex. The information display area 1210 may display information regarding driving conditions of the activation transducer. For example, the information display area 1210 may display text indicating that the depth of the ultrasound image is 12 mm. For example, the information display area 1210 may display text indicating that a frequency used for transmission/reception by the activation transducer is 12 MHz.

The image display area 1220 may display an ultrasound image. The image display area 1220 may display an ultrasound image obtained using the activation transducer displayed on the information display area 1210. The image display area 1220 may display an ultrasound image obtained under the driving conditions displayed on the information display area 1210. For example, the image display area 1220 may display an ultrasound image having a depth of 12 mm.

The guidance window 1230 may be a window notifying that a function of setting the activation transducer array has been executed. The guidance window 1230 may be formed to overlap the image display area 1220. For example, the guidance window 1230 may be formed in a left lower portion of the image display area 1220. The guidance window 1230 may provide information indicating that the activation transducer array is automatically selected based on the setting value of the ultrasound image. For example, the guidance window 1230 may display a guiding phrase "Optimizing." Thus, a user may know that the ultrasound imaging system 100 is automatically selecting the activation transducer array, based on the setting value of the ultrasound image.

The ultrasound imaging system 100 may terminate a function of setting the activation transducer array, in response to a function termination input received through a guidance window. For example, the ultrasound imaging system 100 may terminate a function of setting the activation transducer array, in response to an input of clicking a guidance window. Accordingly, when the user does not wish for the ultrasound imaging system 100 to automatically select the activation transducer array, the user may conveniently terminate the function of setting the activation transducer array.

Figure 13:
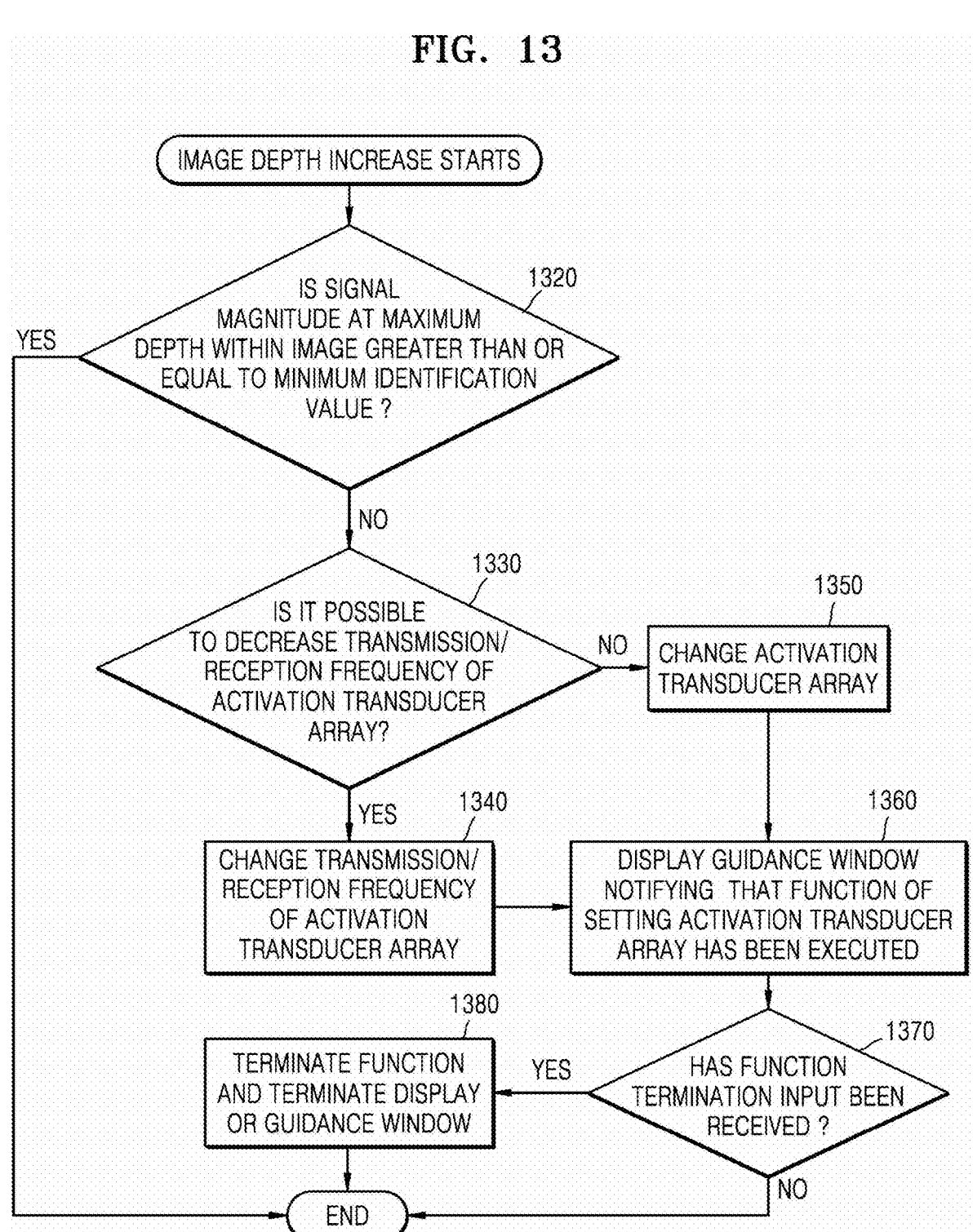
FIG. 13 is a flowchart of a process, performed by an ultrasound imaging system according to an embodiment, of setting a frequency spectrum or an activation transducer array when changing the depth of an ultrasound image.

FIG. 13 is a flowchart of a process, performed by the ultrasound imaging system 100 according to an embodiment, of setting a frequency spectrum or an activation transducer array when changing the depth of an ultrasound image. FIG. 13 may begin in a situation when the ultrasound imaging system 100 receives a user input of increasing the depth of an ultrasound image.

In operation 1320, the ultrasound imaging system 100 according to an embodiment may identify whether a signal magnitude at a maximum depth within the ultrasound image is greater than or equal to a minimum identification value. The minimum identification value may be a minimum value capable of identifying an ultrasound image generated using a signal. For example, the minimum identification value may be –20 dB. When the signal magnitude at a maximum depth within the ultrasound image is greater than or equal to the minimum identification value (operation 1320—YES), the ultrasound imaging system 100 may terminate the process of setting the activation transducer array. When the signal magnitude at a maximum depth within the ultrasound image is less than the minimum identification value (operation 1320—NO), the ultrasound imaging system 100 may proceed to operation 1330.

In operation 1330, the ultrasound imaging system 100 according to an embodiment may identify whether it is possible to decrease the transmission/reception frequency of the activation transducer array. The activation transducer array may have a designated frequency band. For example, a convex transducer array may have a first frequency band and a linear transducer array may have a second frequency band. The ultrasound imaging system 100 may proceed to operation 1340 when it is possible to decrease the transmission/reception frequency of the activation transducer array (operation 1330—YES). The ultrasound imaging system 100 may proceed to operation 1350 when it is not possible to decrease the transmission/reception frequency of the activation transducer array (operation 1330—NO).

In operation 1340, the ultrasound imaging system 100 according to an embodiment may change the transmission/reception frequency of the activation transducer array. When the ultrasound imaging system 100 is able to decrease the transmission/reception frequency of the activation transducer array, the ultrasound imaging system 100 may change the transmission/reception frequency of the activation transducer array while maintaining the activation transducer array. For example, when the depth is 8 mm, the ultrasound imaging system 100 may change the transmission/reception frequency of the activation transducer array to 6 MHz while maintaining the linear transducer array as the activation transducer array.

In operation 1350, the ultrasound imaging system 100 according to an embodiment may change the activation transducer array. When the ultrasound imaging system 100 is unable to decrease the transmission/reception frequency of the activation transducer array, the ultrasound imaging system 100 may automatically change the activation transducer array. For example, when the depth is 12 mm, the ultrasound imaging system 100 may change the activation transducer array from the linear transducer array to the convex transducer array.

In operation 1360, the ultrasound imaging system 100 according to an embodiment may display a guidance window notifying that a function of setting an activation transducer array has been executed. The ultrasound imaging system 100 may provide information that a function of automatically selecting an activation transducer array is being executed, through the guidance window. For example, the ultrasound imaging system 100 may display a guiding phrase "Optimizing" through the guidance window.

In operation 1370, the ultrasound imaging system 100 according to an embodiment may identify whether a function termination input has been received. The ultrasound imaging system 100 may identify whether a function termination input has been received, through the information window. For example, the ultrasound imaging system 100 may identify whether an input of clicking the information window has been received. The ultrasound imaging system 100 may proceed to operation 1380 when the function termination input has been received (operation 1370—YES). When the function termination input has not been received (operation 1370—NO), the ultrasound imaging system 100 may maintain a state of continuously executing the function of setting the activation transducer array.

In operation 1380, the ultrasound imaging system 100 according to an embodiment may terminate the function of setting the activation transducer array. The ultrasound imaging system 100 may terminate the function of setting the activation transducer array, in response to the function termination input. The ultrasound imaging system 100 may terminate display of the guidance window notifying that the function of setting an activation transducer array has been executed.

Figure 14:
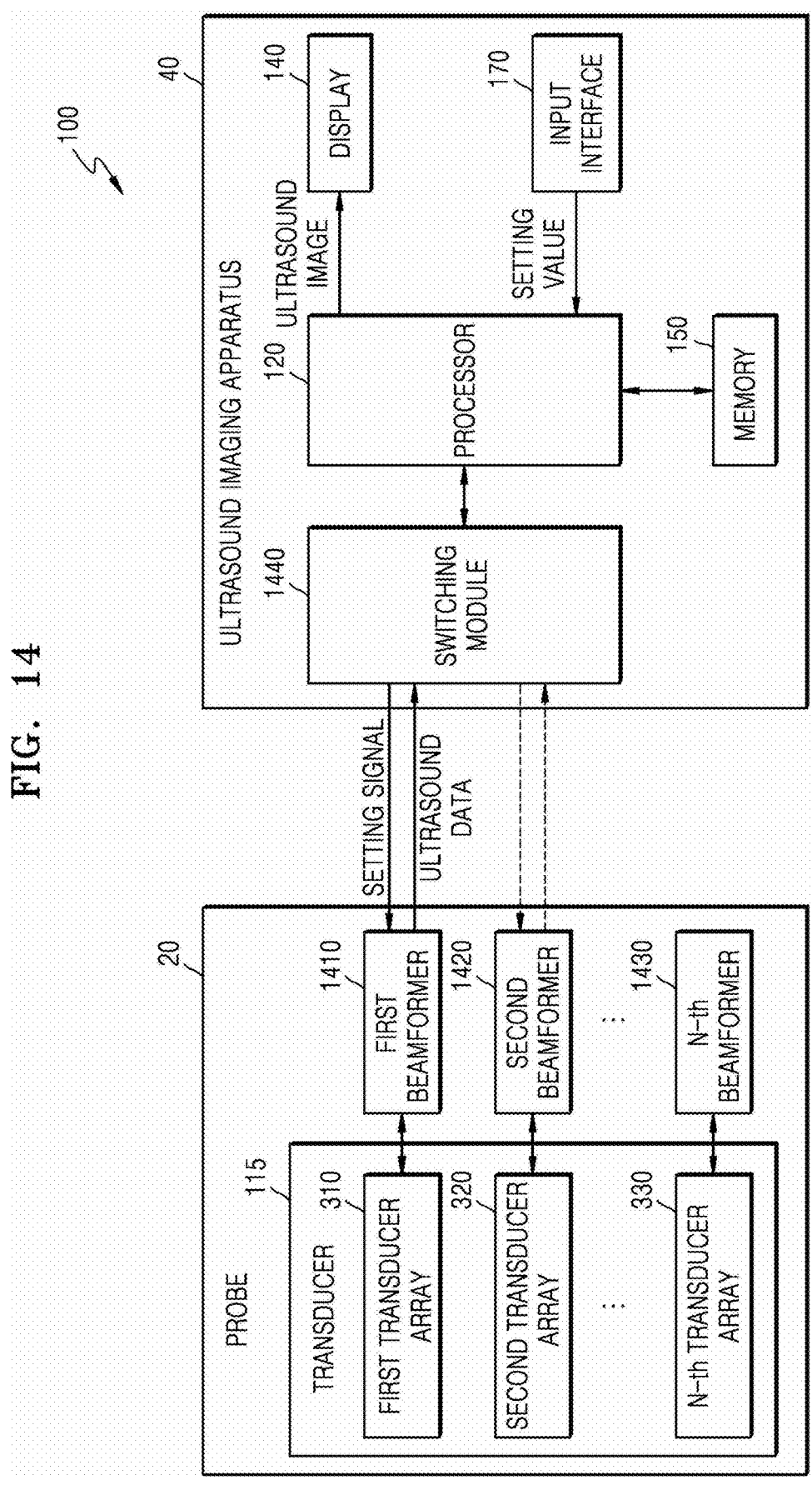
FIG. 14 is a block diagram of an ultrasound imaging system according to an embodiment.

FIG. 14 is a block diagram of the ultrasound imaging system 100 according to an embodiment. The ultrasound imaging system 100 according to an embodiment may include a first beamformer 1410, a second beamformer 1420, . . . , and an N-th beamformer 1430 (where N is a natural number equal to or greater than 3). The ultrasound imaging system 100 according to an embodiment may include a switching module 1440.

The first beamformer 1410 may be connected to the first transducer array 310. The first beamformer 1410 may receive a setting signal from the ultrasound imaging apparatus 40. The first beamformer 1410 may transmit the setting signal to the first transducer array 310. The first beamformer 1410 may receive ultrasound data from the first transducer array 310. The first beamformer 1410 may transmit the ultrasound data to the ultrasound imaging apparatus 40.

The second beamformer 1420 may be connected to the second transducer array 320. The second beamformer 1420 may receive the setting signal from the ultrasound imaging apparatus 40. The second beamformer 1420 may transmit the setting signal to the second transducer array 320. The second beamformer 1420 may receive the ultrasound data from the second transducer array 320. The second beamformer 1420 may transmit the ultrasound data to the ultrasound imaging apparatus 40.

The N-th beamformer 1430 may be connected to an N-th transducer array 330. The N-th beamformer 1430 may receive the setting signal from the ultrasound imaging apparatus 40. The N-th beamformer 1430 may transmit the setting signal to the N-th transducer array 330. The N-th beamformer 1430 may receive the ultrasound data from the N-th transducer array 330. The N-th beamformer 1430 may transmit the ultrasound data to the ultrasound imaging apparatus 40.

The switching module 1440 may receive the setting signal from the processor 120. The switching module 1440 may transmit the setting signal to an activation transducer array set by the processor 120 among the first transducer array 310, the second transducer array 320, and the N-th transducer array 330. The switching module 1440 may transmit the setting signal to at least one of the first beamformer 1410, the second beamformer 1420, and the N-th beamformer 1430. For example, when the processor 120 sets the first transducer array 310 as the activation transducer array, the switching module 1440 may transmit the setting signal to the first beamformer 1410. The switching module 1440 may transmit the setting signal to the first beamformer 1410 so that the first beamformer 1410 transmits the setting signal to the first transducer array 310. The switching module 1440 may transmit the setting signal to the first beamformer 1410 so that the first transducer array 310 obtains the ultrasound data. The switching module 1440 may receive the ultrasound data from the first beamformer 1410.

Figure 15:
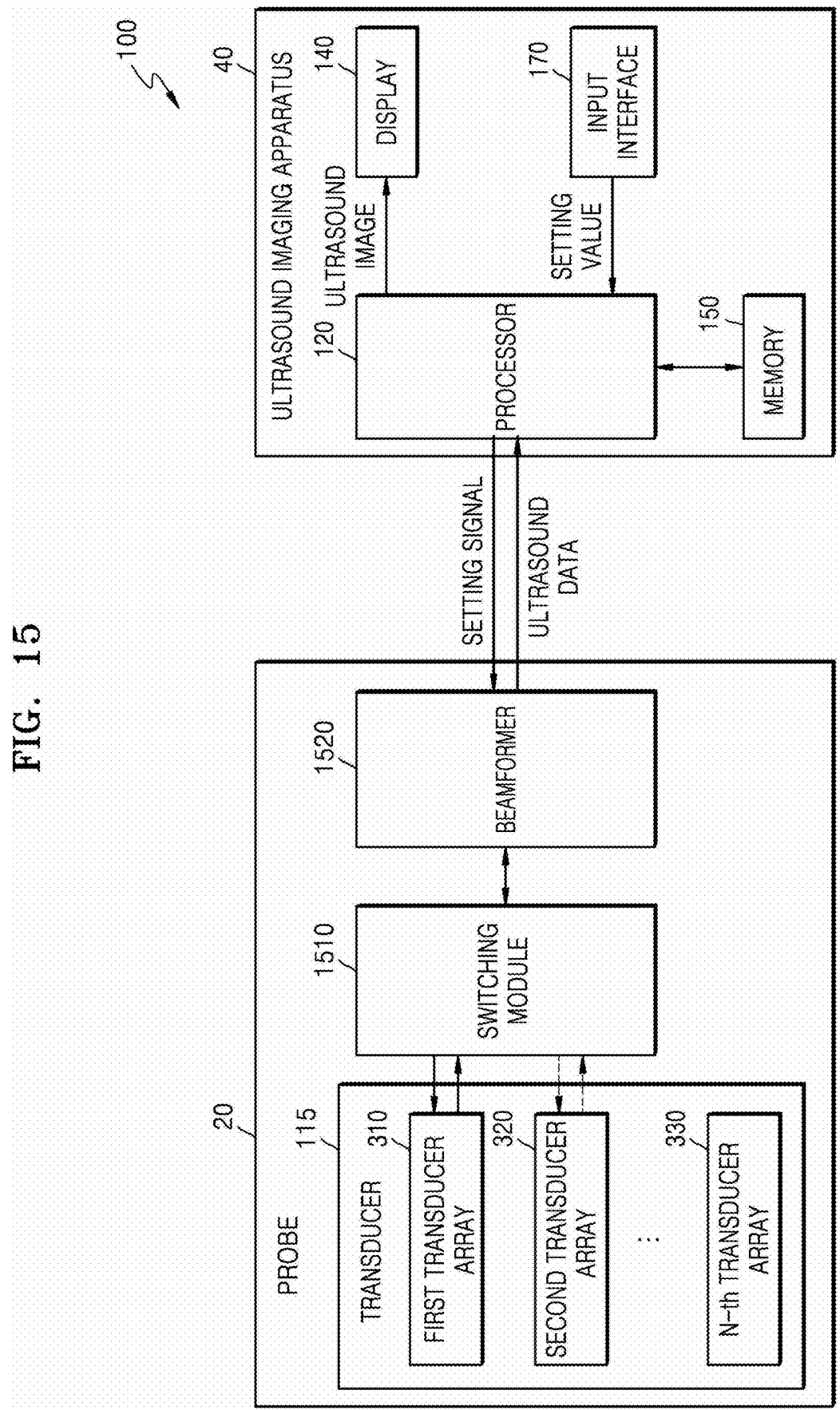
FIG. 15 is a block diagram of an ultrasound imaging system according to an embodiment.

FIG. 15 is a block diagram of the ultrasound imaging system 100 according to an embodiment. The ultrasound imaging system 100 according to an embodiment may include a switching module 1510 and a beamformer 1520.

The switching module 1510 may receive a setting signal from the beamformer 1520. The switching module 1510 may be connected to the first transducer array 310, the second transducer array 320, and the N-th transducer array 330. The switching module 1510 may transmit the setting signal to at least one of the first transducer array 310, the second transducer array 320, and the N-th transducer array 330. The switching module 1510 may receive the ultrasound data from at least one of the first transducer array 310, the second transducer array 320, and the N-th transducer array 330. The switching module 1510 may transmit the ultrasound data to the beamformer 1520.

The beamformer 1520 may receive the setting signal from the processor 120. The beamformer 1520 may transmit the setting signal to the switching module 1510. The beamformer 1520 may receive the ultrasound data from the switching module 1510. The beamformer 1520 may transmit the ultrasound data to the processor 120.

The disclosure provides an ultrasound imaging system having improving performance by displaying an ultrasound image by setting an activation transducer array that automatically obtains ultrasound data in accordance with a setting value of the ultrasound image, a method of controlling the ultrasound imaging system, and a probe included in the ultrasound imaging system. In detail, the disclosure seeks to improve a user convenience of manipulating ultrasound images by setting an activation transducer array based on image setting information worked by the user and automatically optimizing ultrasound image settings to display an ultrasound image.

An ultrasound imaging system according to an embodiment may include a first transducer array and a second transducer array having different specifications, a display configured to display an ultrasound image, based on ultrasound data received through at least one of the first transducer array and the second transducer array, an input interface configured to receive a user input related to a setting value of the ultrasound image, and a processor. The processor may identify the setting value of the ultrasound image included in the user input, set an activation transducer array used to generate the ultrasound image among the first transducer array and the second transducer array, based on the setting value, receive the ultrasound data through the activation transducer array, and control the display to display the ultrasound image by using the ultrasound data.

The first transducer array and the second transducer array may have central axes parallel to each other and transmit transmission signals in same directions.

The setting value may include at least one of the magnification ratio of the ultrasound image, the depth of the ultrasound image, and the location of a region of interest of the ultrasound image.

When the magnification ratio is no less than a minimum change value and less than a first threshold value, the processor may change a transmission/reception frequency of the activation transducer array, and, when the magnification ratio is no less than the first threshold value, the processor may change the activation transducer array.

The processor may change the activation transducer array, based on the setting value, and set a transmission parameter and a reception parameter such that the degree of change in the ultrasound image is maintained within a threshold range before and after the activation transducer array is changed.

The transmission parameter may include at least one of a transmission waveform, a transmission frequency, and the number of transmissions, and the reception parameter may include at least one of a reception waveform, a reception frequency, a gain, and a dynamic range.

The processor may set the transmission parameter and the reception parameter by using at least one of a correlation coefficient of the ultrasound image, a bias value of the ultrasound image, and artificial intelligence that analyzes the ultrasound image, before and after the activation transducer array is changed.

The processor may control the display to display a guidance window indicating that a function of setting the activation transducer array has been executed.

The first transducer array may have a first structure among a plurality of structures. The second transducer array may have a second structure among the plurality of structures. The plurality of structures may include a lead zirconate titanate (PZT)-based piezoelectric structure, a single crystal-based piezoelectric structure, a polymer-based piezoelectric structure, a structure using a piezoelectric composite, a capacitive micromachined ultrasonic transducer (cMUT) structure using micro-electromagnetic system (MEMS) technology, and a piezoelectric micromachined ultrasonic transducer (pMUT) structure using MEMS technology.

The ultrasound imaging system may further include a first beamformer connected to the first transducer array, a second beamformer connected to the second transducer array, and a switching module configured to receive the ultrasound data by transmitting a setting signal to at least one of the first beamformer and the second beamformer.

The ultrasound imaging system may further include a switching module configured to receive the ultrasound data by transmitting a setting signal to at least one of the first transducer array and the second transducer array, and a beamformer configured to transmit the setting signal from the processor to the switching module and transmit the ultrasound data from the switching module to the processor.

A method of controlling an ultrasound imaging system, according to an embodiment, may include receiving a user input related to a setting value of an ultrasound image, identifying the setting value of the ultrasound image included in the user input, setting an activation transducer array used to generate the ultrasound image among a first transducer array and a second transducer array having different specifications, based on the setting value, receiving ultrasound data through the activation transducer array, and displaying the ultrasound image by using the ultrasound data.

The setting of the activation transducer array may include, when the magnification ratio is no less than a minimum change value and less than a first threshold value, changing a transmission/reception frequency of the activation transducer array, and, when the magnification ratio is no less than the first threshold value, changing the activation transducer array.

The setting of the activation transducer array may include changing the activation transducer array, based on the setting value, and setting a transmission parameter and a reception parameter such that the degree of change in the ultrasound image is maintained within a threshold range before and after the activation transducer array is changed.

The setting of the transmission parameter and a reception parameter may include setting the transmission parameter and the reception parameter by using at least one of a correlation coefficient of the ultrasound image, a bias value of the ultrasound image, and artificial intelligence that analyzes the ultrasound image, before and after the activation transducer array is changed.

The setting of the activation transducer array may include displaying a guidance window indicating that a function of setting the activation transducer array has been executed, and terminating the function in response to a function termination input received through the guidance window.

A probe according to an embodiment may include a first transducer array, a second transducer array having a different specification from the first transducer array, and a processor. The processor may receive a setting signal from an ultrasound imaging apparatus that displays an ultrasound image, identify a setting value of the ultrasound image included in the setting signal, set an activation transducer array used to generate the ultrasound image among the first transducer array and the second transducer array, based on the setting value, receive ultrasound data through the activation transducer array, and transmit the ultrasound data to the ultrasound imaging apparatus.

The first transducer array and the second transducer array may be arranged parallel to each other and transmit transmission signals in the same directions.

In an ultrasound imaging system, a method of controlling the ultrasound imaging system, and a probe included in the ultrasound imaging system, performance of displaying an ultrasound image may be improved by setting an activation transducer array that automatically obtains ultrasound data in accordance with a setting value of the ultrasound image.

An apparatus, method, or computer program according to an embodiment perform an operation related to artificial intelligence (AI). An operation related to AI is executed through a processor and a memory. The processor may perform the operation related to AI by using one processor or a plurality of processors. The one or plurality of processors may be a general-purpose processor such as a central processing unit (CPU), an application processor (AP), or a digital signal processor (DSP), a graphics-only processor such as a graphics processing unit (GPU) or a vision processing unit (VPU), or an artificial intelligence (AI)-only processor such as a neural processing unit (NPU). The one or plurality of processors process input data, according to a program, instruction, or AI model stored in memory.

The program, instruction, or AI model related to AI may be created through machine learning. Here, being created through learning means that a basic AI model is trained using a plurality of training data by a learning algorithm, so that a program, instruction, or AI model performing desired characteristics (or a desired purpose) is created. Such learning may be performed in a device itself on which an AI operation according to an embodiment is performed, or may be performed through a separate server and/or system. Examples of the learning algorithm include, but are not limited to, supervised learning, unsupervised learning, semi-supervised learning, or reinforcement learning.

The AI model may be composed of a plurality of neural network layers. Each of the plurality of neural network layers has a plurality of weight values, and performs a neural network operation through an operation between an operation result of a previous layer and the plurality of weight values. The plurality of weight values of the plurality of neural network layers may be optimized by a learning result of the AI model. An artificial neural network may include a deep neural network (DNN), for example, a Convolutional Neural Network (CNN), a Deep Neural Network (DNN), a Recurrent Neural Network (RNN), a Restricted Boltzmann Machine (RBM), a Deep Belief Network (DBN), a Bidirectional Recurrent Deep Neural Network (BRDNN), or a Deep Q-Networks, but embodiments of the disclosure are not limited thereto.

The machine-readable storage medium may be provided as a non-transitory storage medium. The 'non-transitory storage medium' is a tangible device and only means that it does not contain a signal (e.g., electromagnetic waves). This term does not distinguish a case in which data is stored semi-permanently in a storage medium from a case in which data is temporarily stored. For example, the non-transitory recording medium may include a buffer in which data is temporarily stored.

According to an embodiment, methods according to embodiments may be provided by being included in a computer program product. The computer program product, which is a commodity, may be traded between sellers and buyers. Computer program products are distributed in the form of device-readable storage media (e.g., compact disc read only memory (CD-ROM)), or may be distributed (e.g., downloaded or uploaded) through an application store or between two user devices (e.g., smartphones) directly and online. In the case of online distribution, at least a portion of the computer program product (e.g., a downloadable app) may be stored at least temporarily in a device-readable storage medium, such as a memory of a manufacturer's server, a server of an application store, or a relay server, or may be temporarily generated.

What is claimed is:

1. An ultrasound imaging system comprising:
   a first transducer array and a second transducer array,
      wherein the first transducer array and the second transducer array differ in at least one of a shape, a transmission parameter or a reception parameter;

a display configured to display an ultrasound image, based on ultrasound data received through at least one of the first transducer array and the second transducer array;

an input interface configured to receive a user input related to a setting value of the ultrasound image, the setting value related to displaying the ultrasound image; and a processor, wherein the processor is configured to:

identify the setting value of the ultrasound image included in the user input;

set an activation transducer array used to generate the ultrasound image among the first transducer array and the second transducer array, based on the setting value, wherein the setting value comprises at least one of a magnification ratio of the ultrasound image and a location of a region of interest of the ultrasound image;

receive the ultrasound data through the activation transducer array; and control the display to display the ultrasound image by using the ultrasound data, wherein the first transducer array and the second transducer array have central axes parallel to each other and transmit transmission signals in same directions, and wherein the processor is further configured to automatically change the activation transducer array by analyzing image performance changed by user manipulation.

2. The ultrasound imaging system of claim 1, wherein the setting value further includes a depth of the ultrasound image.

3. The ultrasound imaging system of claim 2, wherein the processor is further configured to, when the magnification ratio is equal to or greater than a minimum change value and less than a first threshold value, change a transmission/reception frequency of the activation transducer array, and, when the magnification ratio is equal to or greater than the first threshold value, change the activation transducer array from the first transducer array to the second transducer array or from the second transducer array to the first transducer array.

4. The ultrasound imaging system of claim 1, wherein the processor is further configured to:

change the activation transducer array from the first transducer array to the second transducer array or from the second transducer array to the first transducer array, based on the setting value; and automatically adjust the transmission parameter and the reception parameter such that a degree of change in the ultrasound image is maintained within a threshold range before and after the activation transducer array is changed.

5. The ultrasound imaging system of claim 4, wherein the transmission parameter includes at least one of a transmission waveform, a transmission frequency, and the number of transmissions, and the reception parameter includes at least one of a reception waveform, a reception frequency, a gain, and a dynamic range.

6. The ultrasound imaging system of claim 4, wherein the processor sets the transmission parameter and the reception parameter by using at least one of a correlation coefficient between a reference image and the ultrasound image, a bias value indicating error of the ultrasound image, and artificial intelligence that analyzes the ultrasound image, having the ultrasound image as input, and having the transmission parameter and the reception parameter as output, before and after the activation transducer array is changed.

7. The ultrasound imaging system of claim 1, wherein the processor controls the display to display a guidance window indicating that a function of setting the activation transducer array has been executed.

8. The ultrasound imaging system of claim 1, wherein the first transducer array has a first structure among a plurality of structures, the second transducer array has a second structure among the plurality of structures, and the plurality of structures include a lead zirconate titanate (PZT)-based piezoelectric structure, a single crystal-based piezoelectric structure, a polymer-based piezoelectric structure, a structure using a piezoelectric composite, a capacitive micromachined ultrasonic transducer (cMUT) structure using microelectromagnetic system (MEMS) technology, and a piezoelectric micromachined ultrasonic transducer (pMUT) structure using MEMS technology.

9. The ultrasound imaging system of claim 1, further comprising:

a first beamformer connected to the first transducer array;

a second beamformer connected to the second transducer array; and a switching module configured to receive the ultrasound data by transmitting a setting signal to at least one of the first beamformer and the second beamformer.

10. The ultrasound imaging system of claim 1, further comprising:

a switching module configured to receive the ultrasound data by transmitting a setting signal to at least one of the first transducer array and the second transducer array; and a beamformer configured to transmit the setting signal from the processor to the switching module and transmit the ultrasound data from the switching module to the processor.

11. A method of controlling an ultrasound imaging system, the method comprising:

receiving a user input related to a setting value of an ultrasound image, the setting value related to displaying the ultrasound image;

identifying the setting value of the ultrasound image included in the user input;

setting an activation transducer array used to generate the ultrasound image among a first transducer array and a second transducer array, based on the setting value, wherein the setting value comprises at least one of a magnification ratio of the ultrasound image and a location of a region of interest of the ultrasound image;

receiving ultrasound data through the activation transducer array; and displaying the ultrasound image by using the ultrasound data, wherein the first transducer array and the second transducer array have central axes parallel to each other and transmit transmission signals in same directions, and differ in at least one of a shape, a transmission parameter or a reception parameter, and wherein the processor is further configured to automatically change the activation transducer array by analyzing image performance changed by user manipulation.

12. The method of claim 11, wherein the setting value further includes a depth of the ultrasound image.

13. The method of claim 11, wherein the setting of the activation transducer array comprises:

when the magnification ratio is equal to or greater than a minimum change value and less than a first threshold value, changing a transmission/reception frequency of the activation transducer array; and when the magnification ratio is equal to or greater than the first threshold value, changing the activation transducer array from the first transducer array to the second transducer array or from the second transducer array to the first transducer array.

14. The method of claim 11, wherein the setting of the activation transducer array comprises:

changing the activation transducer array from the first transducer array to the second transducer array or from the second transducer array to the first transducer array, based on the setting value; and automatically adjusting the transmission parameter and the reception parameter such that a degree of change in the ultrasound image is maintained within a threshold range before and after the activation transducer array is changed.

15. The method of claim 14, wherein the transmission parameter includes at least one of a transmission waveform, a transmission frequency, and the number of transmissions, and the reception parameter includes at least one of a reception waveform, a reception frequency, a gain, a dynamic range, the number of scan lines, multiple beams, and synthesis.

16. The method of claim 14, wherein the setting of the transmission parameter and the reception parameter by using at least one of a correlation coefficient between a reference image and the ultrasound image, a bias value indicating error of the ultrasound image, and artificial intelligence that analyzes the ultrasound image, having the ultrasound image as input, and having the transmission parameter and the reception parameter as output, before and after the activation transducer array is changed.

17. The method of claim 11, wherein the setting of the activation transducer array comprises displaying a guidance window indicating that a function of setting the activation transducer array has been executed.

18. A probe comprising:

a first transducer array;

a second transducer array which differs from the first transducer array in at least one of a shape, a transmission parameter or a reception parameter; and a processor, wherein the processor is configured to:

receive a setting signal from an ultrasound imaging apparatus that displays an ultrasound image;

identify a setting value of the ultrasound image included in the setting signal, the setting value related to displaying the ultrasound image;

set an activation transducer array used to generate the ultrasound image among the first transducer array and the second transducer array, based on the setting value, wherein the setting value comprises at least one of a magnification ratio of the ultrasound image and a location of a region of interest of the ultrasound image;

receive ultrasound data through the activation transducer array; and transmit the ultrasound data to the ultrasound imaging apparatus, wherein the first transducer array and the second transducer array have central axes parallel to each other and transmit transmission signals in same directions, and wherein the processor is further configured to automatically change the activation transducer array by analyzing image performance changed by user manipulation.

* * * * *